United States Patent [19]
Vaidya et al.

[11] Patent Number: 5,891,439
[45] Date of Patent: Apr. 6, 1999

[54] LYMPHOCYTE STIMULATING FACTOR

[75] Inventors: Tushar Vaidya, Bandra, India; Abdel-Moiz Bakhiet, Huddinge, Sweden; Tomas Olsson, Alvsjo, Sweden; Krister Kristensson, Bromma, Sweden; John E. Donelson, Iowa City, Iowa

[73] Assignees: SBL Vaccin AB, Stockholm, SE; University of Iowa Research Foundation Inc., Iowa City, both of Iowa

[21] Appl. No.: 686,599

[22] Filed: Jul. 26, 1996

[51] Int. Cl.$^6$ ................... C07K 14/475; C07K 14/52; A61K 38/18; A61K 38/19
[52] U.S. Cl. ................... 424/185.1; 424/198.1; 530/351; 530/399
[58] Field of Search .................. 530/351, 399; 424/185.1, 198.1

[56] References Cited

FOREIGN PATENT DOCUMENTS 0041189  12/1981  European Pat. Off. .
WO 92/18538  10/1992  WIPO .

OTHER PUBLICATIONS

Bakheit et al. Scand J. Immunol. 37: 165–178, Feb. 1993.

*Primary Examiner*—Frank C. Eisenschenk
*Assistant Examiner*—Evelyn Rabin
*Attorney, Agent, or Firm*—Burns, Doane, Swecker & Mathis, L.L.P.

[57] ABSTRACT

Novel polypeptides having lymphocyte stimulating factor activity are disclosed, as well as the use thereof for treating African sleeping sickness. Also, the corresponding nucleic acid sequences are provided as well as truncated forms which encode polypeptides exhibiting enhanced biological activity.

22 Claims, 20 Drawing Sheets

FIG. 1A

```
TATATTGACT GCATCGTGGC GTACCCCGTA GGCTCTTCTC GTTTTTGAAT GTCACCACGG      60
ACCGGTGCTG AGCGCGGAGG AAGGAGAAAG TCAGTCAAGG CCCCGCCACC AGTTGATCCT     120
CTAGTGGAGC TCACAACTTT AGAATCGGTT CATGACGCGT TGGCGAAGGC CGAGCGACTT     180
CGGAACTACT TCCAGGTAGA GCGTGACAAG GTGAATGACT TCTGGACGAT TACAAAGGGG     240
GAGGTGGAGA CTTATCGCAA TCGGCTGTTC AATGCGGAGG CGAGCATTGA AGAACTGGAG     300
CGGTCACACC AGGTAGAGAT GAAGGTATAC AAGCAGAGGG TGCGTCACCT CATCTATGAG     360
CGGAAGAAGA AGGCGCAGGC GTGCCAGGAT GAAAGTCACC GTCTGCTTCG CGAGGCGGAA     420
GACCGGCACC TCCAGCGCAT GAATGAGATA CAGGCTAAGC TCCAACAGCA AGACCAGCAG     480
CTCCGGGCAG CAGCGGCTGA CCATGAAATG AACGTGTACG AGAAGCGCGA TTCGCACAGC     540
TACATGGTAA CCGTTACAAA AACACAGAGT CATGAAAAGG AGCTCGCGCG ACTGCAGGTA     600
TCCTGTGAGG CCAAGTTAAA AGTGTTGCGG GATGAACTGG AGTTAAGACG CCGTCGCCAG     660
ATTCATGAGA TTGAAGAAAG AAAGAATGAG CACATAAACG CCCTCATTAA GCAGCATGAA     720
GAGAAATTTC ATGAAATGAA GACATACTAC AACCAAATAA CCACAAATAA CCTAGAAATC     780
ATTCATTCCT TAAAGGAAGA AATAGCGCAG ATGAAGCAGA ACGACGAGCA TAATGAGACT     840
TTAATGTATG ATATTGATCG GGAGAATCAA AATCTTGTTG CACCGTTAGA AGAAGCTCAG     900
CGTGAGGTTG CGGAGCTGCA GCAGAAACGG AAGCAGAATG AACAGAACAA GCGGGGTCTC     960
GAGGTCACTC GTGTTAAGTT AAGGTCGTTG CGTGAGGAGA TTCGCCGACA GCGTGAAGAA    1020
CATCAGGCCT TGGAGGAGCG TTACGCCTGC GTGCACCGGG AGCGCGAGGA GCTCAAGGGG    1080
AAGTTTGAGT CCGCGCTCCG GCAAGCGGTG ATGGTAGTCG AGGAGCGCAA TGAGGTTCTC    1140
CAGCAAAAGC TTATCGAGTC TCACGCTCTT GTAGAGGAAA GGGATGTACA ACTTGAAGGT    1200
GTTTTGCGCG CCATGAACCCT CGAACCAAAG ACGCTGGAAC TCATCGCGAC TGAGGTCGAC    1260
GAATGGCTTC AACGAAAAAA TCAACTGATA AAAGACTTAC ACTTTGAGCT TAAGAAAGGA    1320
GAAAAGTTGT ACAGCGCGAC GTTGCTCGAG ATGGAGAGCG TTGCCAGACG GCTAACATTG    1380
CTTCACTGCC ACGTAGCAAC TTTGAGTAGG TGTTGTGGTT CACACGTTGG TTGTTCCAAG    1440
TTACGGCTTT GTTGCAGCTC GCATTCGGCC GTGGGCGTGG TGGGCTGTTT TTTTTTTTCT    1500
TCTGTCCTGT TGCCTCTTTC CCCTTTCTAG TGGGCCACTG CGCTTCCTAT GGACCTGTGA    1560
ATGTAGAACT ACGCGTCACA CGCCTTGGTA TGTATGTTGT TACGTGCCGG ATATAGAGAC    1620
AGTTGCTGCT GCGACGAGCG TCGTTGTGAG ACGCGTGAGT GATTGCGAGG CGAAACCTAT    1680
AAAGATTGAG GCCGGTTATC ATTTGTAACCT CACTTTATTG TCATTTCACT AAAAAAAAAA    1740
AAAAAAAAAA                                                           1750
```

FIG. 1B-1

| | | | | | | | | | | | | | | | | |
|---|---|---|---|---|---|---|---|---|---|---|---|---|---|---|---|---|
| TAT | ATT | GAC | TGC | ATC | GTG | GCG | TAC | CCC | GTA | GGC | TCT | TCT | CGT | TTT | TGA | 48 |
| Tyr 1 | Ile | Asp | Cys | Ile 5 | Val | Ala | Tyr | Pro | Val 10 | Gly | Ser | Ser | Arg | Phe 15 | * | |
| ATG | TCA | CCA | CGG | ACC | GGT | GCT | GAG | CGC | GGA | GGA | AGG | AGA | AAG | TCA | GTC | 96 |
| Met | Ser | Pro | Arg 20 | Thr | Gly | Ala | Glu | Arg 25 | Gly | Gly | Arg | Arg | Lys 30 | Ser | Val | |
| AAG | GCC | CCG | CCA | CCA | GTT | GAT | CCT | CTA | GTG | GAG | CTC | ACA | ACT | TTA | GAA | 144 |
| Lys | Ala | Pro 35 | Pro | Pro | Val | Asp | Pro 40 | Leu | Val | Glu | Leu | Thr 45 | Thr | Leu | Glu | |
| TCG | GTT | CAT | GAC | GCG | TTG | GCG | AAG | GCC | GAG | CGA | CTT | CGG | AAC | TAC | TTC | 192 |
| Ser | Val 50 | His | Asp | Ala | Leu | Ala 55 | Lys | Ala | Glu | Arg | Leu 60 | Arg | Asn | Tyr | Phe | |
| CAG | GTA | GAG | CGT | GAC | AAG | GTG | AAT | GAC | TTC | TGG | ACG | ATT | ACA | AAG | GGG | 240 |
| Gln 65 | Val | Glu | Arg | Asp | Lys 70 | Val | Asn | Asp | Phe | Trp 75 | Thr | Ile | Thr | Lys | Gly 80 | |
| GAG | GTG | GAG | ACT | TAT | CGC | AAT | CGG | CTG | TTC | AAT | GCG | GAG | GCG | AGC | ATT | 288 |
| Glu | Val | Glu | Thr | Tyr 85 | Arg | Asn | Arg | Leu | Phe 90 | Asn | Ala | Glu | Ala | Ser 95 | Ile | |
| GAA | GAA | CTG | GAG | CGG | TCA | CAC | CAG | GTA | GAG | ATG | AAG | GTA | TAC | AAG | CAG | 336 |
| Glu | Glu | Leu | Glu 100 | Arg | Ser | His | Gln | Val 105 | Glu | Met | Lys | Val | Tyr 110 | Lys | Gln | |
| AGG | GTG | CGT | CAC | CTC | ATC | TAT | GAG | CGG | AAG | AAG | AAG | GCG | CAG | GCG | TGC | 384 |
| Arg | Val | Arg 115 | His | Leu | Ile | Tyr | Glu 120 | Arg | Lys | Lys | Lys | Ala 125 | Gln | Ala | Cys | |
| CAG | GAT | GAA | AGT | CAC | CGT | CTG | CTT | CGC | GAG | GCG | GAA | GAC | CGG | CAC | CTC | 432 |
| Gln | Asp 130 | Glu | Ser | His | Arg | Leu 135 | Leu | Arg | Glu | Ala | Glu 140 | Asp | Arg | His | Leu | |
| CAG | CGC | ATG | AAT | GAG | ATA | CAG | GCT | AAG | CTC | CAA | CAG | CAA | GAC | CAG | CAG | 480 |
| Gln | Arg | Met | Asn | Glu 150 | Ile | Gln | Ala | Lys | Leu | Gln 155 | Gln | Gln | Asp | Gln | Gln 160 | |
| | | | | | | | | | | | | | | | | |
| | | | | | | | | | | | | | | | | |
| CTC | CGG | GCA | GCA | GCG | GCT | GAC | CAT | GAA | ATG | AAC | GTG | TAC | GAG | AAG | CGC | 528 |
| Leu | Arg | Ala | Ala | Ala 165 | Ala | Asp | His | Glu | Met 170 | Asn | Val | Tyr | Glu | Lys 175 | Arg | |
| GAT | TCG | CAC | AGC | TAC | ATG | GTA | ACC | GTT | ACA | AAA | ACA | CAG | AGT | CAT | GAA | 576 |
| Asp | Ser | His | Ser 180 | Tyr | Mer | Val | Thr | Val 185 | Thr | Lys | Thr | Gln | Ser 190 | His | Glu | |
| AAG | GAG | CTC | GCG | CGA | CTG | CAG | GTA | TCC | TGT | GAG | GCC | AAG | TTA | AAA | GTG | 624 |
| Lys | Glu | Leu | Ala | Arg 195 | Leu | Gln | Val | Ser 200 | Cys | Glu | Ala | Lys 205 | Leu | Lys | Val | |
| TTG | CGG | GAT | GAA | CTG | GAG | TTA | AGA | CGC | CGT | CGC | CAG | ATT | CAT | GAG | ATT | 672 |
| Leu | Arg 210 | Asp | Glu | Leu | Glu | Leu 215 | Arg | Arg | Arg | Arg | Gln 220 | Ile | His | Glu | Ile | |
| GAA | GAA | AGA | AAG | AAT | GAG | CAC | ATA | AAC | GCC | CTC | ATT | AAG | CAG | CAT | GAA | 720 |
| Glu 225 | Glu | Arg | Lys | Asn | Glu 230 | His | Ile | Asn | Ala | Leu 235 | Ile | Lys | Gln | His | Glu 240 | |

FIG. 1B-2

| | | | | | | | | | | | | | | | | |
|---|---|---|---|---|---|---|---|---|---|---|---|---|---|---|---|---|
| GAG | AAA | TTT | CAT | GAA | ATG | AAG | ACA | TAC | TAC | AAC | CAA | ATA | ACC | ACA | AAT | 768 |
| Glu | Lys | Phe | His | Glu | Met | Lys | Thr | Thr | Tyr | Asn | Gln | Ile | Thr | Thr | Asn | |
| | | | | 245 | | | | | 250 | | | | | 255 | | |
| AAC | CTA | GAA | ATC | ATT | CAT | TCC | TTA | AAG | GAA | GAA | ATA | GCG | CAG | ATG | AAG | 816 |
| Asn | Leu | Glu | Ile | Ile | His | Ser | Leu | Lys | Glu | Glu | Ile | Ala | Gln | Met | Lys | |
| | | | 260 | | | | | 265 | | | | | 270 | | | |
| CAG | AAC | GAC | GAG | CAT | AAT | GAG | ACT | TTA | ATG | TAT | GAT | ATT | GAT | CGG | GAG | 864 |
| Gln | Asn | Asp | Glu | His | Asn | Glu | Thr | Leu | Met | Tyr | Asp | Ile | Asp | Arg | Glu | |
| | | 275 | | | | | 280 | | | | | 285 | | | | |
| AAT | CAA | AAT | CTT | GTT | GCA | CCG | TTA | GAA | GAA | GCT | CAG | CGT | GAG | GTT | GCG | 912 |
| Asn | Gln | Asn | Leu | Val | Ala | Pro | Leu | Glu | Glu | Ala | Gln | Arg | Glu | Val | Ala | |
| | 290 | | | | | 295 | | | | | 300 | | | | | |
| GAG | CTG | CAG | CAG | AAA | CGG | AAG | CAG | AAT | GAA | CAG | AAC | AAG | CGG | GGT | CTC | 960 |
| Glu | Leu | Gln | Gln | Lys | Arg | Lys | Gln | Asn | Glu | Gln | Asn | Lys | Arg | Gly | Leu | |
| 305 | | | | | 310 | | | | | 315 | | | | | 320 | |
| GAG | GTC | ACT | CGT | GTT | AAG | TTA | AGG | TCG | TTG | CGT | GAG | GAG | ATT | CGC | CGA | 1008 |
| Glu | Val | Thr | Arg | Val | Lys | Leu | Arg | Ser | Leu | Arg | Glu | Glu | Ile | Arg | Arg | |
| | | | | 325 | | | | | 330 | | | | | 335 | | |
| CAG | CGT | GAA | GAA | CAT | CAG | GCC | TTG | GAG | GAG | CGT | TAC | GCC | TGC | GTG | CAC | 1056 |
| Gln | Arg | Glu | Glu | His | Gln | Ala | Leu | Glu | Glu | Arg | Tyr | Ala | Cys | Val | His | |
| | | | 340 | | | | | 345 | | | | | 350 | | | |
| CGG | GAG | CGC | GAG | GAG | CTC | AAG | GGG | AAG | TTT | GAG | TCC | GCG | CTC | CGG | CAA | 1104 |
| Arg | Glu | Arg | Glu | Glu | Leu | Lys | Gly | Lys | Phe | Glu | Ser | Ala | Leu | Arg | Gln | |
| | | 355 | | | | | 360 | | | | | 365 | | | | |
| GCG | GTG | ATG | GTA | GTC | GAG | GAG | CGC | AAT | GAG | GTT | CTC | CAG | CAA | AAG | CTT | 1152 |
| Ala | Val | Met | Val | Val | Glu | Glu | Arg | Asn | Glu | Val | Leu | Gln | Gln | Lys | Leu | |
| | 370 | | | | | 375 | | | | | 380 | | | | | |
| ATC | GAG | TCT | CAC | GCT | CTT | GTA | GAG | GAA | AGG | GAT | GTA | CAA | CTT | GAA | GGT | 1200 |
| Ile | Glu | Ser | His | Ala | Leu | Val | Glu | Glu | Arg | Asp | Val | Gln | Leu | Glu | Gly | |
| 385 | | | | | 390 | | | | | 395 | | | | | 400 | |
| GTT | TTG | CGC | GCC | ATG | AAC | CTC | GAA | CCA | AAG | ACG | CTG | GAA | CTC | ATC | GCG | 1248 |
| Val | Leu | Arg | Ala | Met | Asn | Leu | Glu | Pro | Lys | Thr | Leu | Glu | Leu | Ile | Ala | |
| | | | | 405 | | | | | 410 | | | | | 415 | | |
| ACT | GAG | GTC | GAC | GAA | TGG | CTT | CAA | CGA | AAA | AAT | CAA | CTG | ATA | AAA | GAC | 1296 |
| Thr | Glu | Val | Asp | Glu | Trp | Leu | Gln | Arg | Lys | Asn | Gln | Leu | Ile | Lys | Asp | |
| | | | 420 | | | | | 425 | | | | | 430 | | | |
| TTA | CAC | TTT | GAG | CTT | AAG | AAA | GGA | GAA | AAG | TTG | TAC | AGC | GCG | ACG | TTG | 1344 |
| Leu | His | Phe | Glu | Leu | Lys | Lys | Gly | Glu | Lys | Leu | Tyr | Ser | Ala | Thr | Leu | |
| | | 435 | | | | | 440 | | | | | 445 | | | | |
| CTC | GAG | ATG | GAG | AGC | GTT | GCC | AGA | CGG | CTA | ACA | TTG | CTT | CAC | TGC | CAC | 1392 |
| Leu | Glu | Met | Glu | Ser | Val | Ala | Arg | Arg | Leu | Thr | Leu | Leu | His | Cys | His | |
| | 450 | | | | | 455 | | | | | 460 | | | | | |
| GTA | GCA | ACT | TTG | AGT | AGG | TGT | TGT | GGT | TCA | CAC | GTT | GGT | TGT | TCC | AAG | 1440 |
| Val | Ala | Thr | Leu | Ser | Arg | Cys | Cys | Gly | Ser | His | Val | Gly | Cys | Ser | Lys | |
| 465 | | | | | 470 | | | | | 475 | | | | | 480 | |

FIG. 1B-3

| | | | | | | | | | | | | | | | | |
|---|---|---|---|---|---|---|---|---|---|---|---|---|---|---|---|---|
| TTA | CGG | CTT | TGT | TGC | AGC | TCG | CAT | TCG | GCC | GTG | GGC | GTG | GTG | GGC | TGT | 1488 |
| Leu | Arg | Leu | Cys | Cys | Ser | Ser | His | Ser | Ala | Val | Gly | Val | Val | Gly | Cys | |
| | | | | 485 | | | | | 490 | | | | | 495 | | |
| TTT | TTT | TTT | TCT | TCT | GTC | CTG | TTG | CCT | CTT | TCC | CCT | TTC | TAG | TGG | GCC | 1536 |
| Phe | Phe | Phe | Ser | Ser | Val | Leu | Leu | Pro | Leu | Ser | Pro | Phe | * | Trp | Ala | |
| | | | 500 | | | | | 505 | | | | | 510 | | | |
| ACT | GCG | CTT | CCT | ATG | GAC | CTG | TGA | ATG | TAG | AAC | TAC | GCG | TCA | CAC | GCC | 1584 |
| Thr | Ala | Leu | Pro | Met | Asp | Leu | * | Met | * | Asn | Tyr | Ala | Ser | His | Ala | |
| | | 515 | | | | | 520 | | | | | 525 | | | | |
| TTG | GTA | TGT | ATG | TTG | TTA | CGT | GCC | GGA | TAT | AGA | GAC | AGT | TGC | TGC | TGC | 1632 |
| Leu | Val | Cys | Met | Leu | Leu | Arg | Ala | Gly | Tyr | Arg | Asp | Ser | Cys | Cys | Cys | |
| | 530 | | | | | 535 | | | | | 540 | | | | | |
| GAC | GAG | CGT | CGT | TGT | GAG | ACG | CGT | GAG | TGA | TTG | CGA | GGC | GAA | ACC | TAT | 1680 |
| Asp | Glu | Arg | Arg | Cys | Glu | Thr | Arg | Glu | * | Leu | Arg | Gly | Glu | Thr | Tyr | |
| 545 | | | | | 550 | | | | | 555 | | | | | 560 | |
| AAA | GAT | TGA | GGC | CGG | TTA | TCA | TTG | TAA | CCT | CAC | TTT | ATT | GTC | ATT | TCA | 1728 |
| Lys | Asp | * | Gly | Arg | Leu | Ser | Leu | * | Pro | His | Phe | Ile | Val | Ile | Ser | |
| | | | | 565 | | | | | 570 | | | | | 575 | | |
| CTA | AAA | AAA | AAA | AAA | AAA | AAA | A | | | | | | | | | 1750 |
| Leu | Lys | Lys | Lys | Lys | Lys | Lys | | | | | | | | | | |
| | | | 580 | | | | | | | | | | | | | |

FIG. 1C-1

| | | | | | | | | | | | | | | |
|---|---|---|---|---|---|---|---|---|---|---|---|---|---|---|
| Tyr 1 | Ile | Asp | Cys | Ile 5 | Val | Ala | Tyr | Pro | Val 10 | Gly | Ser | Ser | Arg | Phe 15 | * |
| Met | Ser | Pro | Arg 20 | Thr | Gly | Ala | Glu | Arg 25 | Gly | Gly | Arg | Arg | Lys 30 | Ser | Val |
| Lys | Ala | Pro 35 | Pro | Pro | Val | Asp | Pro 40 | Leu | Val | Glu | Leu | Thr 45 | Thr | Leu | Glu |
| Ser | Val 50 | His | Asp | Ala | Leu | Ala 55 | Lys | Ala | Glu | Arg | Leu 60 | Arg | Asn | Tyr | Phe |
| Gln 65 | Val | Glu | Arg | Asp | Lys 70 | Val | Asn | Asp | Phe | Trp 75 | Thr | Ile | Thr | Lys | Gly 80 |
| Glu | Val | Glu | Thr | Tyr 85 | Arg | Asn | Arg | Leu | Phe 90 | Asn | Ala | Glu | Ala | Ser 95 | Ile |
| Glu | Glu | Leu | Glu 100 | Arg | Ser | His | Gln | Val 105 | Glu | Met | Lys | Val | Tyr 110 | Lys | Gln |
| Arg | Val | Arg 115 | His | Leu | Ile | Tyr | Glu 120 | Arg | Lys | Lys | Lys | Ala 125 | Gln | Ala | Cys |
| Gln | Asp 130 | Glu | Ser | His | Arg | Leu 135 | Leu | Arg | Glu | Ala | Glu 140 | Asp | Arg | His | Leu |
| Gln 145 | Arg | Met | Asn | Glu | Ile 150 | Gln | Ala | Lys | Leu | Gln 155 | Gln | Gln | Asp | Gln | Gln 160 |
| Leu | Arg | Ala | Ala | Ala 165 | Ala | Asp | His | Glu | Met 170 | Asn | Val | Tyr | Glu | Lys 175 | Arg |
| Asp | Ser | His | Ser 180 | Tyr | Met | Val | Thr | Val 185 | Thr | Lys | Thr | Gln | Ser 190 | His | Glu |
| Lys | Glu | Leu 195 | Ala | Arg | Leu | Gln | Val 200 | Ser | Cys | Glu | Ala | Lys 205 | Leu | Lys | Val |
| Leu | Arg 210 | Asp | Glu | Leu | Glu | Leu 215 | Arg | Arg | Arg | Arg | Gln 220 | Ile | His | Glu | Ile |
| Glu 225 | Glu | Arg | Lys | Asn | Glu 230 | His | Ile | Asn | Ala | Leu 235 | Ile | Lys | Gln | His | Glu 240 |
| Glu | Lys | Phe | His | Glu 245 | Met | Lys | Thr | Tyr | Tyr 250 | Asn | Gln | Ile | Thr | Thr 255 | Asn |
| Asn | Leu | Glu | Ile 260 | Ile | His | Ser | Leu | Lys 265 | Glu | Glu | Ile | Ala | Gln 270 | Met | Lys |

FIG. 1C-2

Gln Asn Asp Glu His Asn Glu Thr Leu Met Tyr Asp Ile Asp Arg Glu
        275             280                 285

Asn Gln Asn Leu Ala Ala Pro Leu Glu Glu Ala Gln Arg Glu Val Ala
    290             295                 300

Glu Leu Gln Gln Lys Arg Lys Gln Asn Glu Gln Asn Lys Arg Gly Leu
305             310             315                     320

Glu Val Thr Arg Val Lys Leu Arg Ser Leu Arg Glu Glu Ile Arg Arg
                325             330                 335

Gln Arg Glu Glu His Gln Ala Leu Glu Glu Arg Tyr Ala Cys Val His
            340             345                 350

Arg Glu Arg Glu Glu Leu Lys Gly Lys Phe Glu Ser Ala Leu Arg Gln
        355             360                 365

Ala Val Met Val Val Glu Glu Arg Asn Glu Val Leu Gln Gln Lys Leu
    370             375             380

Ile Glu Ser His Ala Leu Val Glu Glu Arg Asp Val Gln Leu Glu Gly
385             390             395                     400

Val Leu Arg Ala Met Asn Leu Glu Pro Lys Thr Leu Glu Leu Ile Ala
            405             410                 415

Thr Glu Val Asp Glu Trp Leu Gln Arg Lys Asn Gln Leu Ile Lys Asp
            420             425                 430

Leu His Phe Glu Leu Lys Lys Gly Glu Lys Leu Tyr Ser Ala Thr Leu
        435             440             445

Leu Glu Met Glu Ser Val Ala Arg Arg Leu Thr Leu Leu His Cys His
    450             455             460

Val Ala Thr Leu Ser Arg Cys Cys Gly Ser His Val Gly Cys Ser Lys
465             470             475                 480

Leu Arg Leu Cys Cys Ser Ser His Ser Ala Val Gly Val Val Gly Cys
            485             490             495

Phe Phe Phe Ser Ser Val Leu Leu Pro Leu Ser Pro Phe * Trp Ala
        500             505             510

Thr Ala Leu Pro Met Asp Leu * Met * Asn Tyr Ala Ser His Ala
        515             520                 525

Leu Val Cys Met Leu Leu Arg Ala Gly Tyr Arg Asp Ser Cys Cys Cys
    530             535             540

Asp Glu Arg Arg Cys Glu Thr Arg Glu * Leu Arg Gly Glu Thr Tyr
545             550                 555                     560

Lys Asp * Gly Arg Leu Ser Leu * Pro His Phe Ile Val Ile Ser
            565             570                 575

Leu Lys Lys Lys Lys Lys Lys
            580

FIG. 1D-1

| | | | | | | | | | | | | | | |
|---|---|---|---|---|---|---|---|---|---|---|---|---|---|---|
| Met 1 | Ser | Pro | Arg | Thr 5 | Gly | Ala | Glu | Arg | Gly 10 | Gly | Arg | Arg | Lys | Ser 15 | Val |
| Lys | Ala | Pro | Pro 20 | Pro | Val | Asp | Pro | Leu 25 | Val | Glu | Leu | Thr | Thr 30 | Leu | Glu |
| Ser | Val | His 35 | Asp | Ala | Leu | Ala | Lys 40 | Ala | Glu | Arg | Leu | Arg 45 | Asn | Tyr | Phe |
| Gln | Val 50 | Glu | Arg | Asp | Lys | Val 55 | Asn | Asp | Phe | Trp | Thr 60 | Ile | Thr | Lys | Gly |
| Glu 65 | Val | Glu | Thr | Tyr | Arg 70 | Asn | Arg | Leu | Phe | Asn 75 | Ala | Glu | Ala | Ser | Ile 80 |
| Glu | Glu | Leu | Glu | Arg 85 | Ser | His | Gln | Val | Glu 90 | Met | Lys | Val | Tyr | Lys 95 | Gln |
| Arg | Val | Arg | His 100 | Leu | Ile | Tyr | Glu | Arg 105 | Lys | Lys | Lys | Ala | Gln 110 | Ala | Cys |
| Gln | Asp | Glu 115 | Ser | His | Arg | Leu | Leu 120 | Arg | Glu | Ala | Glu | Asp 125 | Arg | His | Leu |
| Gln | Arg 130 | Met | Asn | Glu | Ile | Gln 135 | Ala | Lys | Leu | Gln | Gln 140 | Gln | Asp | Gln | Gln |
| Leu 145 | Arg | Ala | Ala | Ala | Ala 150 | Asp | His | Glu | Met | Asn 155 | Val | Tyr | Glu | Lys | Arg 160 |
| Asp | Ser | His | Ser | Tyr 165 | Met | Val | Thr | Val | Thr 170 | Lys | Thr | Gln | Ser | His 175 | Glu |
| Lys | Glu | Leu | Ala 180 | Arg | Leu | Gln | Val | Ser 185 | Cys | Glu | Ala | Lys | Leu 190 | Lys | Val |
| Leu | Arg | Asp 195 | Glu | Leu | Glu | Leu | Arg 200 | Arg | Arg | Arg | Gln | Ile 205 | His | Glu | Ile |
| Glu | Glu 210 | Arg | Lys | Asn | Glu | His 215 | Ile | Asn | Ala | Leu | Ile 220 | Lys | Gln | His | Glu |
| Glu 225 | Lys | Phe | His | Glu | Met 230 | Lys | Thr | Tyr | Tyr | Asn 235 | Gln | Ile | Thr | Thr | Asn 240 |
| Asn | Leu | Glu | Ile | Ile 245 | His | Ser | Leu | Lys | Glu 250 | Glu | Ile | Ala | Gln | Met 255 | Lys |
| Gln | Asn | Asp | Glu 260 | His | Asn | Glu | Thr | Leu 265 | Met | Tyr | Asp | Ile | Asp 270 | Arg | Glu |
| Asn | Gln | Asn 275 | Leu | Val | Ala | Pro | Leu 280 | Glu | Glu | Ala | Gln | Arg 285 | Gly | Val | Ala |
| Glu | Leu 290 | Gln | Gln | Lys | Arg | Lys 295 | Gln | Asn | Glu | Gln | Asn 300 | Lys | Arg | Gly | Leu |

FIG. 1D-2

| | | | | | | | | | | | | | | |
|---|---|---|---|---|---|---|---|---|---|---|---|---|---|---|
| Glu 305 | Val | Thr | Arg | Val | Lys 310 | Leu | Arg | Ser | Leu | Arg 315 | Glu | Glu | Ile | Arg | Arg 320 |
| Gln | Arg | Glu | Glu | His 325 | Gln | Ala | Leu | Glu | Glu 330 | Arg | Tyr | Ala | Cys | Val | His 335 |
| Arg | Glu | Arg | Glu 340 | Glu | Leu | Lys | Gly | Lys 345 | Phe | Glu | Ser | Ala | Leu 350 | Arg | Gln |
| Ala | Val | Met 355 | Val | Val | Glu | Glu | Arg 360 | Asn | Glu | Val | Leu | Gln 365 | Gln | Lys | Leu |
| Ile | Glu 370 | Ser | His | Ala | Leu | Val 375 | Glu | Glu | Arg | Asp | Val 380 | Gln | Leu | Glu | Gly |
| Val 385 | Leu | Arg | Ala | Met | Asn 390 | Leu | Glu | Pro | Lys | Thr 395 | Leu | Glu | Leu | Ile | Ala 400 |
| Thr | Glu | Val | Asp | Glu 405 | Trp | Leu | Gln | Arg | Lys 410 | Asn | Gln | Leu | Ile | Lys 415 | Asp |
| Leu | His | Phe | Glu 420 | Leu | Lys | Lys | Gly | Glu 425 | Lys | Leu | Tyr | Ser | Ala 430 | Thr | Leu |
| Leu | Glu | Met 435 | Glu | Ser | Val | Ala | Arg 440 | Arg | Leu | Thr | Leu | Leu 445 | His | Cys | His |
| Val | Ala 450 | Thr | Leu | Ser | Arg | Cys 455 | Cys | Gly | Ser | His | Val 460 | Gly | Cys | Ser | Lys |
| Leu 465 | Arg | Leu | Cys | Cys | Ser 470 | Ser | His | Ser | Ala | Val 475 | Gly | Val | Val | Gly | Cys 480 |
| Phe | Phe | Phe | Ser | Ser 485 | Val | Leu | Leu | Pro | Leu 490 | Ser | Pro | Phe | | | |

FIG. 1E-1

| | | | | | | | | | | | | | |
|---|---|---|---|---|---|---|---|---|---|---|---|---|---|
| Met 1 | Ser | Pro | Arg | Thr 5 | Gly | Ala | Glu | Arg | Gly 10 | Gly | Arg | Arg | Lys | Ser 15 | Val |
| Lys | Ala | Pro | Pro 20 | Pro | Val | Asp | Pro | Leu 25 | Val | Glu | Leu | Thr | Thr 30 | Leu | Glu |
| Ser | Val | His 35 | Asp | Ala | Leu | Ala | Lys 40 | Ala | Glu | Arg | Leu | Arg 45 | Asn | Tyr | Phe |
| Gln | Val 50 | Glu | Arg | Asp | Lys | Val 55 | Asn | Asp | Phe | Trp | Thr 60 | Ile | Thr | Lys | Gly |
| Glu 65 | Val | Glu | Thr | Tyr | Arg 70 | Asn | Arg | Leu | Phe | Asn 75 | Ala | Glu | Ala | Ser | Ile 80 |
| Glu | Glu | Leu | Glu | Arg 85 | Ser | His | Gln | Val | Glu 90 | Met | Lys | Val | Tyr | Lys 95 | Gln |
| Arg | Val | Arg | His 100 | Leu | Ile | Tyr | Glu | Arg 105 | Lys | Lys | Lys | Ala | Gln 110 | Ala | Cys |
| Gln | Asp | Glu 115 | Ser | His | Arg | Leu | Leu 120 | Arg | Glu | Ala | Glu | Asp 125 | Arg | His | Leu |
| Gln | Arg 130 | Met | Asn | Glu | Ile | Gln 135 | Ala | Lys | Leu | Gln | Gln 140 | Gln | Asp | Gln | Gln |
| Leu 145 | Arg | Ala | Ala | Ala | Ala 150 | Asp | His | Glu | Met | Asn 155 | Val | Tyr | Glu | Lys | Arg 160 |
| Asp | Ser | His | Ser | Tyr 165 | Met | Val | Thr | Val | Thr 170 | Lys | Thr | Gln | Ser | His 175 | Glu |
| Lys | Glu | Leu | Ala 180 | Arg | Leu | Gln | Val | Ser 185 | Cys | Glu | Ala | Lys | Leu 190 | Lys | Val |
| Leu | Arg | Asp 195 | Glu | Leu | Glu | Leu | Arg 200 | Arg | Arg | Arg | Gln | Ile 205 | His | Glu | Ile |
| Glu | Glu 210 | Arg | Lys | Asn | Glu | His 215 | Ile | Asn | Ala | Leu | Ile 220 | Lys | Gln | His | Glu |
| Glu 225 | Lys | Phe | His | Glu | Met 230 | Lys | Thr | Tyr | Tyr | Asn 235 | Gln | Ile | Thr | Thr | Asn 240 |
| Asn | Leu | Glu | Ile | Ile 245 | His | Ser | Leu | Lys | Glu 250 | Glu | Ile | Ala | Gln | Met 255 | Lys |
| Gln | Asn | Asp | Glu 260 | His | Asn | Glu | Thr | Leu 265 | Met | Tyr | Asp | Leu | Asp 270 | Arg | Glu |
| Asn | Gln | Asn 275 | Leu | Val | Ala | Pro | Leu 280 | Glu | Glu | Ala | Gln | Arg 285 | Glu | Val | Ala |
| Glu | Leu 290 | Gln | Gln | Lys | Arg | Lys 295 | Gln | Asn | Glu | Gln | Asn 300 | Lys | Arg | Gly | Leu |

FIG. 1E-2

| | | | | | | | | | | | | | | |
|---|---|---|---|---|---|---|---|---|---|---|---|---|---|---|
| Glu 305 | Val | Thr | Arg | Val | Lys 310 | Leu | Arg | Ser | Leu | Arg 315 | Glu | Glu | Ile | Arg | Arg 320 |

Glu 305 Val Thr Arg Val Lys 310 Leu Arg Ser Leu Arg 315 Glu Glu Ile Arg Arg 320

Gln Arg Glu Glu His 325 Gln Ala Leu Glu Glu 330 Arg Tyr Ala Cys Val 335 His

Arg Glu Arg Glu 340 Glu Leu Lys Gly Lys 345 Phe Glu Ser Ala Leu 350 Arg Gln

Ala Val Met 355 Val Val Glu Glu Arg 360 Asn Glu Val Leu Gln 365 Gln Lys Leu

Ile Glu 370 Ser His Ala Leu Val 375 Glu Glu Arg Asp Val 380 Gln Leu Glu Gly

Val 385 Leu Arg Ala Met Asn 390 Leu Glu Pro Lys Thr 395 Leu Glu Leu Ile Ala 400

Thr Glu Val Asp Glu 405 Trp Leu Gln Arg Lys 410 Asn Gln Leu Ile Lys 415 Asp

Leu His Phe Glu 420 Leu Lys Lys Gly Glu 425 Lys Leu Tyr Ser Ala 430 Thr Leu

Leu Glu Met 435 Glu Ser Val Ala Arg 440 Arg Leu Thr Leu Leu 445 His Cys His

Val Ala 450 Thr Leu Ser Arg Cys 455 Cys Gly Ser His Val 460 Gly Cys Ser Lys

Leu 465 Arg Leu

FIG. 1F-1

| | | | | | | | | | | | | | | |
|---|---|---|---|---|---|---|---|---|---|---|---|---|---|---|
| Met 1 | Ser | Pro | Arg | Thr 5 | Gly | Ala | Glu | Arg | Glu 10 | Gly | Arg | Arg | Lys | Ser 15 | Val |
| Lys | Ala | Pro | Pro 20 | Pro | Val | Asp | Pro | Leu 25 | Val | Glu | Leu | Thr | Thr 30 | Leu | Glu |
| Ser | Val | His 35 | Asp | Ala | Leu | Ala | Lys 40 | Ala | Glu | Arg | Leu | Arg 45 | Asn | Tyr | Phe |
| Gln | Val 50 | Glu | Arg | Asp | Lys | Val 55 | Asn | Asp | Phe | Trp | Thr 60 | Ile | Thr | Lys | Gly |
| Glu 65 | Val | Glu | Thr | Tyr | Arg 70 | Asn | Arg | Leu | Phe | Asn 75 | Ala | Glu | Ala | Ser | Ile 80 |
| Glu | Glu | Leu | Glu | Arg 85 | Ser | His | Gln | Val | Glu 90 | Met | Lys | Val | Tyr | Lys 95 | Gln |
| Arg | Val | Arg | His 100 | Leu | Ile | Tyr | Glu | Arg 105 | Lys | Lys | Lys | Ala | Gln 110 | Ala | Cys |
| Gln | Asp | Glu 115 | Ser | His | Arg | Leu | Leu 120 | Arg | Glu | Ala | Glu | Asp 125 | Arg | His | Leu |
| Gln | Arg 130 | Met | Asn | Glu | Ile | Gln 135 | Ala | Lys | Leu | Gln | Gln 140 | Gln | Asp | Gln | Gln |
| Leu 145 | Arg | Ala | Ala | Ala | Ala 150 | Asp | His | Glu | Met | Asn 155 | Val | Tyr | Glu | Lys | Arg 160 |
| Asp | Ser | His | Ser | Tyr 165 | Met | Val | Thr | Val | Thr 170 | Lys | Thr | Gln | Ser | His 175 | Glu |
| Lys | Glu | Leu | Ala 180 | Arg | Leu | Gln | Val | Ser 185 | Cys | Glu | Ala | Lys | Leu 190 | Lys | Val |
| Leu | Arg | Asp 195 | Glu | Leu | Glu | Leu | Arg 200 | Arg | Arg | Arg | Gln | Ile 205 | His | Glu | Ile |
| Glu | Glu 210 | Arg | Lys | Asn | Glu | His 215 | Ile | Asn | Ala | Leu | Ile 220 | Lys | Gln | His | Glu |
| Glu 225 | Lys | Phe | His | Glu | Met 230 | Lys | Thr | Tyr | Tyr | Asn 235 | Gln | Ile | Thr | Thr | Asn 240 |
| Asn | Leu | Glu | Ile | Ile 245 | His | Ser | Leu | Lys | Glu 250 | Glu | Ile | Ala | Gln | Met 255 | Lys |
| Gln | Asn | Asp | Glu 260 | His | Asn | Glu | Thr | Leu 265 | Met | Tyr | Asp | Ile | Asp 270 | Arg | Glu |

FIG. 1F-2

Asn Gln Asn Leu Val Ala Pro Leu Glu Glu Ala Gln Arg Glu Val Ala
        275                    280                    285

Glu Leu Gln Gln Lys Arg Lys Gln Asn Glu Gln Asn Lys Arg Gly Leu
    290                   295                  300

Glu Val Thr Arg Val Lys Leu Arg Ser Leu Arg Glu Glu Ile Arg Arg
305                   310               315                   320

Gln Arg Glu Glu His Gln Ala Leu Glu Glu Arg Tyr Ala Cys Val His
                325             330                335

Arg Glu Arg Glu Glu Leu Lys Gly Lys Phe Glu Ser Ala Leu Arg Gln
        340                 345                350

Ala Val Met Val Val Glu Glu Arg Asn Glu Val Leu Gln Gln Lys Leu
        355                 360             365

Ile Glu Ser His Ala Leu Val Glu Glu Arg Asp Val Gln Leu Glu Gly
    370                   375             380

Val Leu Arg Ala Met Asn Leu Glu Pro Lys Thr Leu Glu Leu Ile Ala
385                   390               395               400

Thr Glu Val Asp Glu Trp Leu Gln Arg Lys Asn Gln Leu Ile Lys Asp
                405                   410            415

Leu His Phe Glu Leu Lys Lys Gly Glu Lys Leu Tyr Ser Ala Thr Leu
            420                 425               430

Leu Glu Met Glu Ser Val Ala Arg Arg Leu Thr Leu Leu His Cys His
        435                 440             445

Val Ala Thr Leu
450

FIG. 1G

| | | | | | | | | | | | | | | |
|---|---|---|---|---|---|---|---|---|---|---|---|---|---|---|
| Met 1 | Ser | Pro | Arg | Thr 5 | Gly | Ala | Glu | Arg | Gly 10 | Gly | Arg | Arg | Lys | Ser 15 | Val |
| Lys | Ala | Pro | Pro 20 | Pro | Val | Asp | Pro | Leu 25 | Val | Glu | Leu | Thr | Thr 30 | Leu | Glu |
| Ser | Val | His 35 | Asp | Ala | Leu | Ala | Lys 40 | Ala | Glu | Arg | Leu | Arg 45 | Asn | Tyr | Phe |
| Gln | Val 50 | Glu | Arg | Asp | Lys | Val 55 | Asn | Asp | Phe | Trp | Thr 60 | Ile | Thr | Lys | Gly |
| Glu 65 | Val | Glu | Thr | Tyr | Arg 70 | Asn | Arg | Leu | Phe | Asn 75 | Ala | Glu | Ala | Ser | Ile 80 |
| Glu | Glu | Leu | Glu | Arg 85 | Ser | His | Gln | Val | Glu 90 | Met | Lys | Val | Tyr | Lys 95 | Gln |
| Arg | Val | Arg | His 100 | Leu | Ile | Tyr | Glu | Arg 105 | Lys | Lys | Lys | Ala | Gln 110 | Ala | Cys |
| Gln | Asp | Glu 115 | Ser | His | Arg | Leu | Leu 120 | Arg | Glu | Ala | Glu | Asp 125 | Arg | His | Leu |
| Gln | Arg 130 | Met | Asn | Glu | Ile | Gln 135 | Ala | Lys | Leu | Gln | Gln 140 | Gln | Asp | Gln | Gln |
| Leu 145 | Arg | Ala | Ala | Ala | Ala 150 | Asp | His | Glu | Met | Asn 155 | Val | Tyr | Glu | Lys | Arg 160 |
| Asp | Ser | His | Ser | Tyr 165 | Met | Val | Thr | Val | Thr 170 | Lys | Thr | Gln | Ser | His 175 | Glu |
| Lys | Glu | Leu | Ala 180 | Arg | Leu | Gln | Val | Ser 185 | Cys | Glu | Ala | Lys | Ile 190 | Lys | Val |
| Leu | Arg | Asp 195 | Glu | Leu | Glu | Leu | Arg 200 | Arg | Arg | Arg | Gln | Ile 205 | His | Glu | Ile |
| Glu | Glu 210 | Arg | Lys | Asn | Glu | His 215 | Ile | Asn | Ala | Leu | Ile 220 | Lys | Gln | His | Glu |
| Glu 225 | Lys | Phe | His | Glu | Met 230 | Lys | Thr | Tyr | Tyr | Asn 235 | Gln | Ile | Thr | Thr | Asn 240 |
| Asn | Leu | Glu | Ile | Ile 245 | His | Ser | Leu | Lys | Glu 250 | Glu | Ile | Ala | Gln | Met 255 | Lys |
| Gln | Asn | Asp | Glu 260 | His | Asn | Glu | Thr | Leu 265 | Met | Tyr | Asp | Ile | Asp 270 | Arg | Glu |
| Asn | Gln | Asn 275 | Leu | Val | Ala | Pro | Leu 280 | Glu | Glu | Ala | Gln | Arg 285 | Glu | Val | Ala |
| Glu | Leu 290 | Gln | Gln | Lys | Arg | Lys 295 | Gln | Asn | Glu | Gln | Asn 300 | Lys | Arg | Gly | Leu |
| Glu 305 | Val | Thr | Arg | Val | Lys 310 | Leu | | | | | | | | | |

FIG. 1H

| | | | | | | | | | | | | | | |
|---|---|---|---|---|---|---|---|---|---|---|---|---|---|---|
|Met 1|Ser|Pro|Arg|Thr 5|Gly|Ala|Glu|Arg|Gly 10|Gly|Arg|Arg|Lys|Ser 15|Val|
|Lys|Ala|Pro|Pro 20|Pro|Val|Asp|Pro|Leu 25|Val|Glu|Leu|Thr|Thr 30|Leu|Glu|
|Ser|Val|His 35|Asp|Ala|Leu|Ala|Lys 40|Ala|Glu|Arg|Leu|Arg 45|Asn|Tyr|Phe|
|Gln|Val 50|Glu|Arg|Asp|Lys|Val 55|Asn|Asp|Phe|Trp|Thr 60|Ile|Thr|Lys|Gly|
|Glu 65|Val|Glu|Thr|Tyr|Arg 70|Asn|Arg|Leu|Phe|Asn 75|Ala|Glu|Ala|Ser|Ile 80|
|Glu|Glu|Leu|Glu|Arg 85|Ser|His|Gln|Val|Glu 90|Met|Lys|Val|Tyr|Lys 95|Gln|
|Arg|Val|Arg|His 100|Leu|Ile|Tyr|Glu|Arg 105|Lys|Lys|Lys|Ala|Gln 110|Ala|Cys|
|Gln|Asp|Glu 115|Ser|His|Arg|Leu|Leu 120|Arg|Glu|Ala|Glu|Asp 125|Arg|His|Leu|
|Gln|Arg 130|Met|Asn|Glu|Ile|Gln 135|Ala|Lys|Leu|Gln|Gln 140|Gln|Asp|Gln|Gln|
|Leu 145| | | | | | | | | | | | | | |

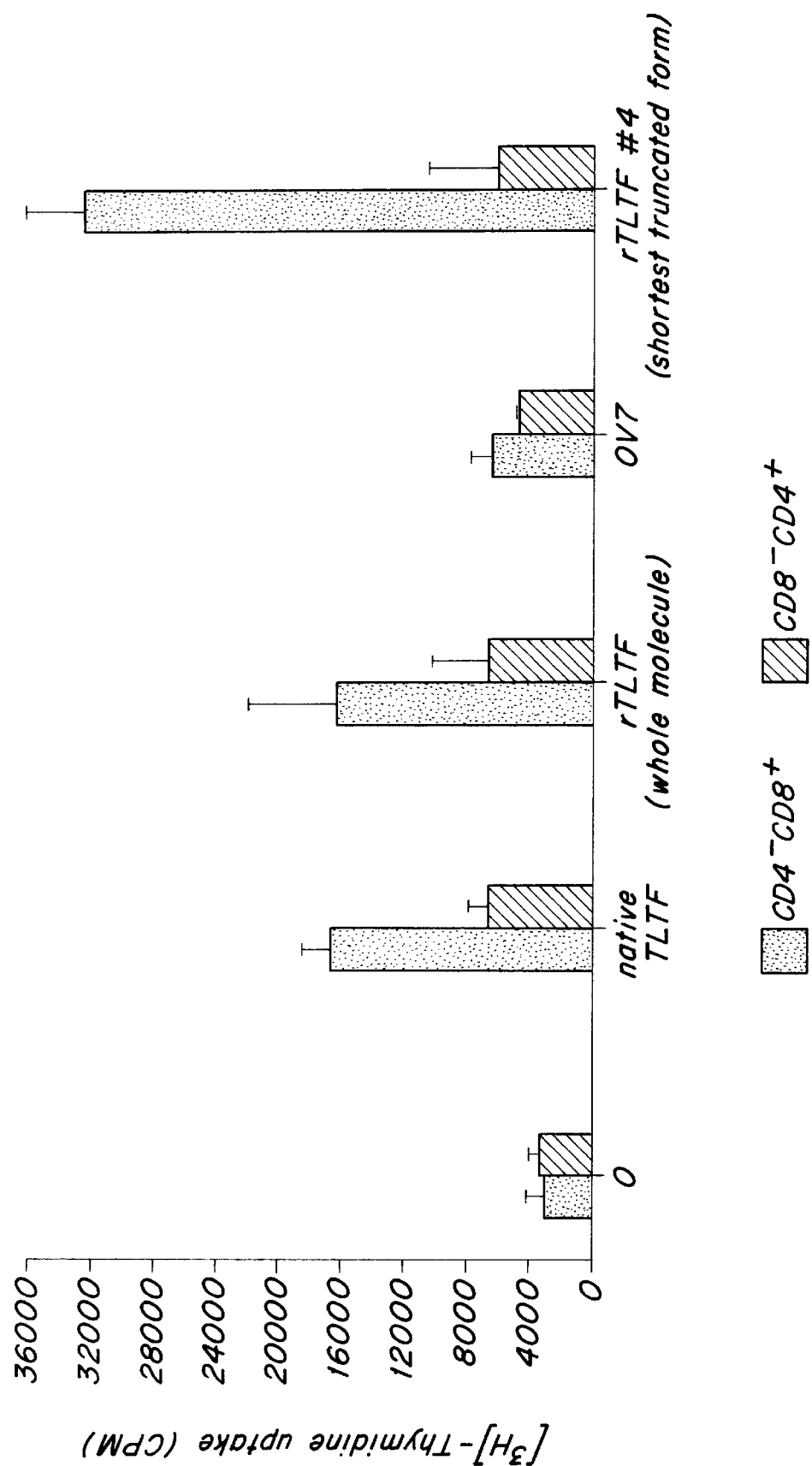

LYMPHOCYTE STIMULATING FACTOR

INTRODUCTION

The present invention relates to a lymphocyte triggering factor, which has the ability to stimulate CD8+ T cells in a living body. The invention also relates to a nucleotide sequense coding for said lymphocyte triggering factor as well as a monoclonal antibody directed against said factor.

BACKGROUND

African Trypanosomiasis is a disease widespread in the tropical Africa. It exists in (i) humans as Sleeping Sickness, caused by *Trypanosoma brucei gambiense* (*T.b. gambiense*) or *T.b. rhodesiense*, (ii) in cattle as Nagana caused by *T. congolense* and *T. vivax* and (iii) in camels as Surra and caused by *T. evansi*. Mortality is caused either by massive parasitosis or secondary infections due to immunosuppression, which is an important trait of the disease (Werry et al., 1982, Askonas,B. A. "Interference in general immune function by parasite infections; African trypanosomiasis as a model system", Parasitology 1984; 88:633–638). Existing therapies are either cumbersome or toxic and there is no available vaccine. Furthermore, methods for diagnosing the disease are poorly developed.

A new principle for how a microorganism may subvert the host defense has been detected using an experimental model for African tryptanosomiasis where rodents have been infected with *T.b. brucei*. The studies focused on CD8+T cells and interferon gamma (IFN-$\gamma$) as putative important host derived elements in the interactions with the parasite during infection. IFN-$\gamma$ production in the spleen increased markedly early after infection (Bakhiet,M., Olsson, T., Van der Meide, P., and Kristensson, K., "Depletion of CD8+ T cells suppresses growth of *T. brucei brucei* and IFN-$\gamma$ production in infected rats", Clin Exp Immunol 1990; 81: 195–199). Both in vivo monoclonal antibody CD8+T cell depleted rats, as well as genomically CD8 deleted mice, showed absence of IFN-$\gamma$ induction, dramatically decreased parasitaemia and prolonged survival (Bakhiet et al., 1990, supra, Olsson, T., Bakhiet, M., Höjeberg, B., Ljungdahl, Å., Edlund, C., Andersson, G., Ekre, H-P, Fung Leung, W-P, Mak, T., Wigzell, H., Fiszer, U., Kristensson, K., "CD8 is critically involved in lymphocyte activation by a *Trypanosoma brucei brucei* released molecule", Cell 1993; 72:715–727). Also, intraperitoneal injeciton of anti IFN-$\gamma$ antibody suppressed parasite growth and increased survival of the animals (Olsson et al., 1993, supra). In vitro studies showed that the trypanosome released a lymphocyte triggering factor (TLTF), which through binding to CD8 on lymphoid cells, triggers these cells to secrete IFN-$\gamma$, which in turn constitutes a growth stimulus for the parasite (Olsson, T., Bakhiet, M., Edlund, C., Höjeberg, B., Van der Meide, P., and Kristensson, K.,"Bidirectional activating signals between *Trypanosoma brucei* and CD8+ T cells: A trypanosome-released factor triggers interferon gamma production that stimulate parasite growth", Eur. J. Immunol. 1991; 21:2447–2454; Olsson et al, 1993, supra). A mouse monoclonal antibody (MO1) was raised and used to purify TLTF with affinity chromatography. In addition, passive immunotherapy in vivo with MO1 strongly reduced parasite levels and prolonged survival of the animals (Bakhiet, M., Olsson, T., Edlund, C., Höjeberg, B., Holmberg, K., Lorentzon, J., and Kristensson, K., "A *trypanosoma brucei brucei* derived factor that triggers CD8+ lymphocytes to interferon gamma secretion: Purification, characterization and protective effects in vivo by treatment with a monoclonal antibody against the factor", Scand. J. Immunol. 1993; 37:165–178).

Hitherto, it has not been possible to clone TLTF for the production of recombinant material or peptide parts of the molecule, which could be tested in future vaccination attempts. Had this been possible, the molecule might furthermore be used in the targeting of CD8+ cells both in vivo and in vitro.

GENERAL DESCRIPTION OF THE INVENTION

The present inventors have succeeded in the cloning of TLTF. Thus, this invention relates to a lymphocyte stimulating factor comprising a protein component having the ability to stimulate, in a living animal body, CD8+ T-cells resulting in the release of interferon-$\gamma$ (IFN-$\gamma$) to elicit immunosuppression or immunostimulation in said body.

In addition, the invention relates to a nucleotide sequence coding for said lymphocyte stimulating factor as well as a monoclonal antibody directed against it.

LEGENDS TO THE FIGURES

For a better understanding therof, the present invention will be disclosed under reference to figures. While a more detailed disclosure thereof will be found below, a summary of the figures is as follows:

FIG. 1A depicts SEQ. ID. NO. 1, which is the complete cDNA sequence for TLTF.

FIG. 1B depicts (SEQ. ID. NOS. 2,4,6,8,10,12,14) which is the amino acid translation of the cloned cDNA.

FIG. 1C depicts (SEQ. ID. NOS. 3,5,7,9,11,13,15) which is the protein according to FIG. 1B.

FIG. 1D depicts (SEQ. ID. NO: 16) which is the complete predicted amino acid sequence of TLTF.

FIGS. 1E–H depicts (SEQ. ID. NOS: 17–20) which are the predicted amino acid sequences of four truncations of TLTF according to the invention.

DETAILED DESCRIPTION OF THE INVENTION

Figure 2:
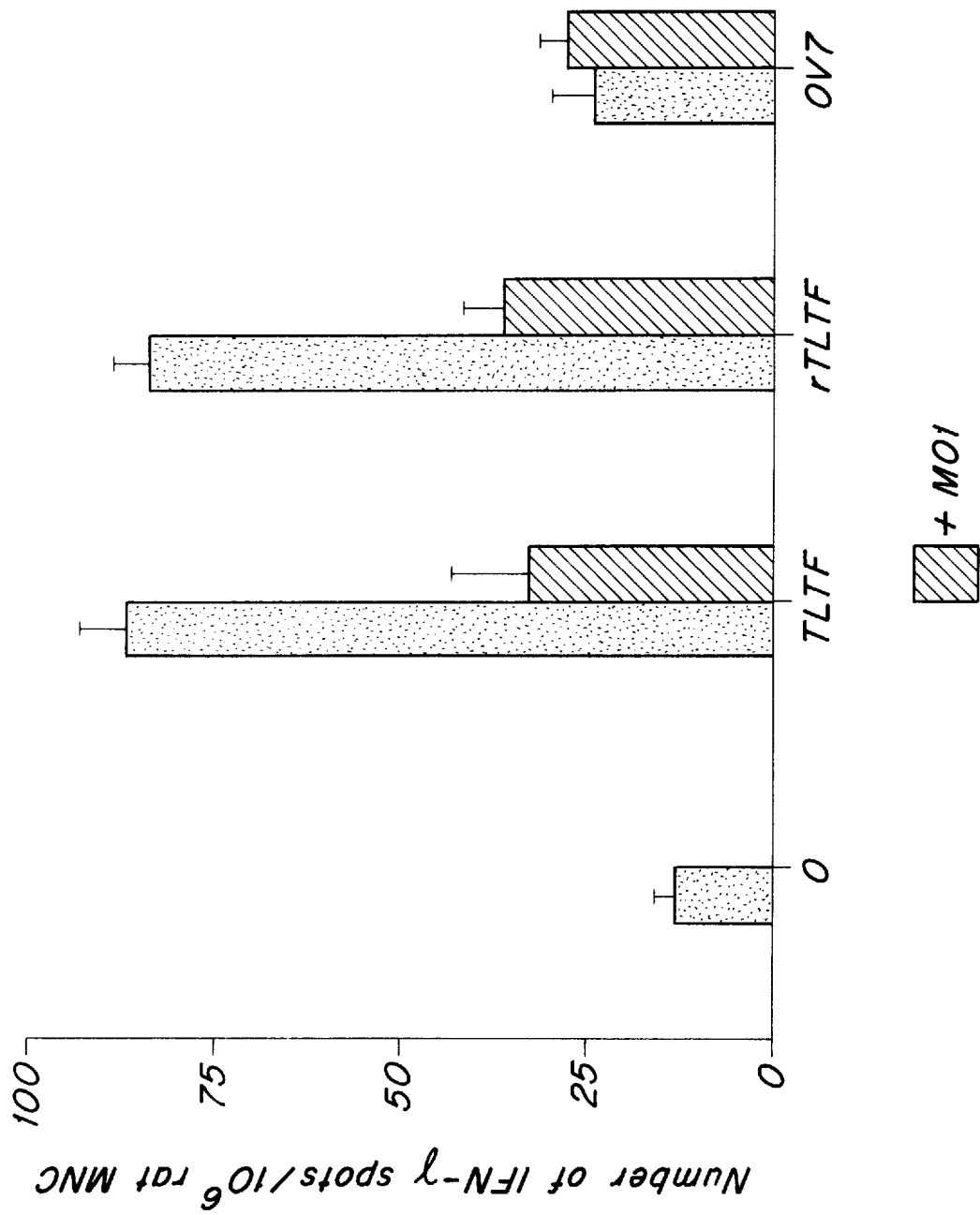
FIG. 2 shows the number of IFN-$\gamma$ secreting cells determined in an immunospot assay by a graph, wherein the number of IFN-$\gamma$ spots/$10^6$ rat MNC are plotted for TLTF, rTLTF and OV7.
Figure 3:
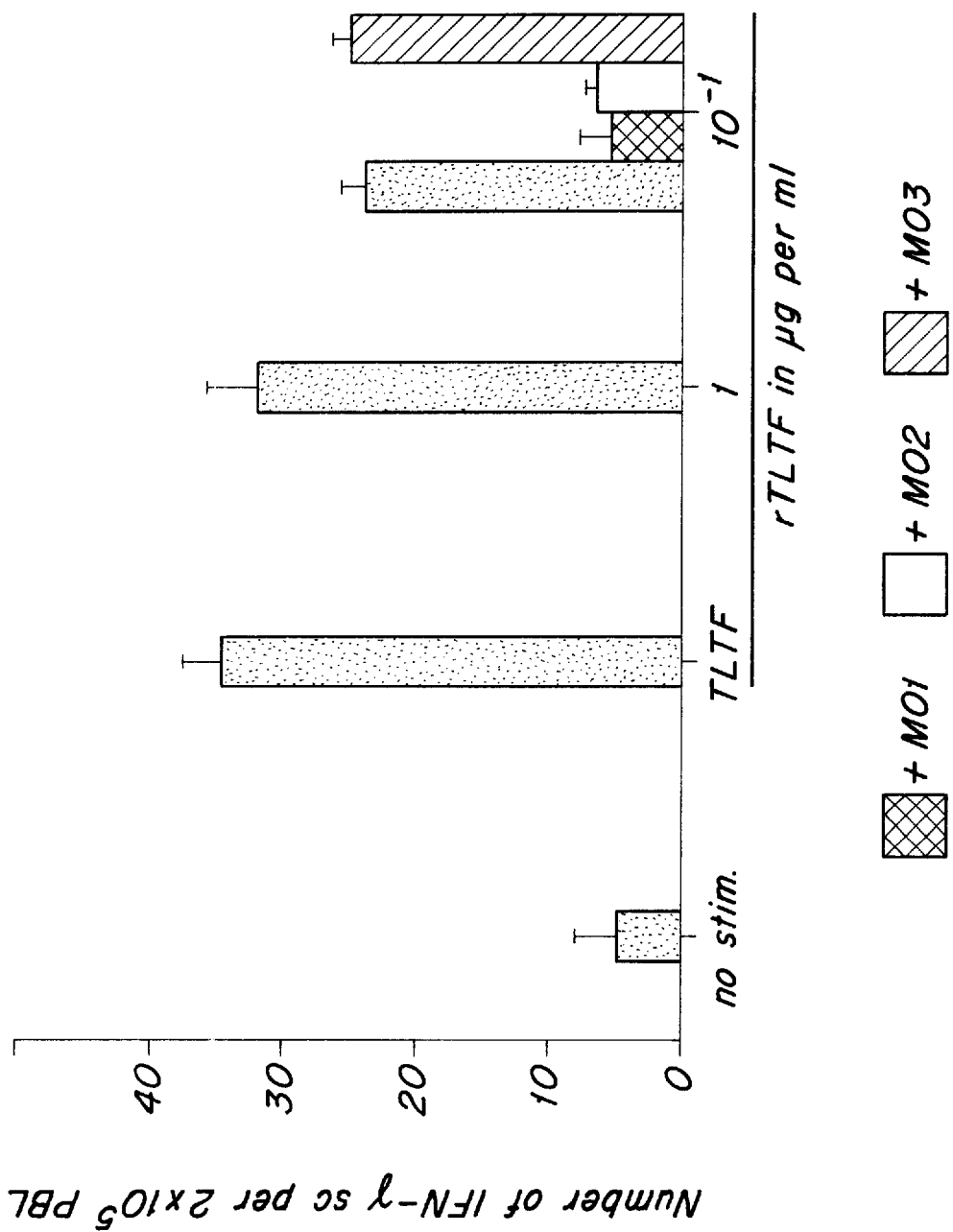
FIG. 3 shows monoclonal anti-TLTF antibodies effect on rTLTF triggering of human peripheral blood (PBL).

The object of the present invention is more specifically a lymphocyte stimulating factor comprising a protein component having the ability to stimulate, in a living animal body, CD8+ T-cells resulting in the release of interferon-$\gamma$ (IFN-$\gamma$) to elicit immunosuppression or immunostimulation in said body, wherein said protein component is selected from amino acid sequences within the sequence of amino acids numbered 1 to about 150 in FIG. 1B, which are in possession of said ability. The amino acid sequence showed no homologies to previously described proteins, and since it represents a non-variable protein it is a potential candidate for immune therapy.

One object of the invention is a lymphocyte stimulating factor, which comprises a protein component consisting of at least about 70 amino acid residues according to FIG. 1B.

Another object of the invention is a lymphocyte stimulating factor, which comprises a protein component consisting of at least about 100 amino acid residues according to FIG. 1B.

Yet another object of the invention is a lymphocyte stimulating factor, which comprises a protein component consisting of at least about 120 amino acid residues according to FIG. 1B.

Further, another object of the present invention is a lymphocyte stimulating factor as defined above, comprising a protein component having the ability to stimulate, in a living animal body, CD8+ T-cells resulting in the release of interferon-γ (IFN-γ) to elicit immunosuppression or immunostimulation in said body, wherein said protein component is selected from amino acid sequences within the sequence of amino acids numbered 1 to about 300 in FIG. 1B.

A further object of the present invention is a lymphocyte stimulating factor as defined above for use as a vaccine against African sleeping sickness.

Another object of the present invention is such a lymphocyte stimulating as is defined above for use in the preparation of an antiserum useful for combatting African sleeping sickness.

Yet another object of the present invention is a nucleotide sequence coding for any of the lymphocyte stimulating factors according to the invention.

Another object of the invention is such a nucleotide sequence, as is shown in FIG. 1A.

Another object of the invention is a monoclonal antibody directed against any one of the lymphocyte stimulating factors according to the invention.

One further object of the present invention is a method of treating African sleeping sickness, comprising the administration to a mammal, including man, in need of such treatment of an effective amount of an antibody against any of the lymphocyte stimulating factors according to the invention, said antibody interacting with said factor released by the parasite causing said sickness.

A further object of the invention is a method of vaccinating a mammal, including man, against African sleeping sickness, comprising the administration to the mammal of an immunologically active amount of any one of the described lymphocyte stimulating factors.

EXPERIMENTAL

MATERIAL AND METHODS

Parasites

The following trypanosome preparations were used in the present work: (a) *T.b. brucei* An Tat 1/1, which was used to generate the native TLTF. The parasites were obtained from Dr. Nestor Van Meirvenne, Laboratory of Serology, Institute of Tropical Medicine, Prins Leopold, Antwerp, Belgium. The parasite were passaged once in rats and purified from infected blood (according to Lanham, S. M., Godfrey, D. G., "Isolation of salivarian trypanosomes from man and other animals using DEAE-cellulose", Exp. Parasitol. 1970; 28:521–534) and then disrupted by freezing and thawing before experimentation. (b) *T.b. rhodesiense* clone MVAT4 Rx (Alarcon, C. M., Son, H. J., Hall, T., and Donelson, J. E., "A monocistronic transcript for a trypanosoma variant surface glycoprotein", Mol. Cell Biol. 1994;14:5579–5591), from which total RNA was isolated to construct the cDNA library.

Animals

Rats and mice were used in this study. SpragueDawley rats were purchased from Alab (Stockholm, Sweden). DBA/2 MHC H-2d/d mice were locally bred at the Department of Immunology, Karolinska Institute, Stockholm. Mutant mice (CD8⁻)with disrupted lyt 2 gene lacking CD8 expression (Fung-Leung, W-P, Schillham, M. W., Rahemtulla, A., Kundig, T. M., Vollenweider, M. J., van Ewijk, W., and Mak, T. W. "CD8 is needed for the development of cytotoxic T cells but not helper T cells", Cell 1991; 443–449), and mutant mouse strain lacking CD4 expression (Rahemtulla A., Fung-Leung W. P., Schillman M. W., Kundig T. M., Sambara S. R., Narendran A., Arabian, A., Wakeham., A., Paige., C. J., Zinkernagel, R. M., Miller, R. G., and Mak, T. W., "Normal development and function of CD8+ cells but markedly decreased helper cell activity in mice lacking CD4", Nature 1991; 353:180–184) originally from Department of Medical Biophysics and Immunology, University of Toronto, Canada, were bred and kept at the Department of Immunology, Karolinska Institute, Stockholm, Sweden).

Antibodies

In in vitro antibody TLTF modulation experiments (see below) the following Mabs were used: (a) IB-4; a Mab directed against TNP (anti-trinitrophenylphosphate) was used as an isotype matched control antibody (mouse IgG2b). The hybridoma producing IB-4 was obtained from Dr. Birgitta Heyman (Uppsala, Sweden), and antibodies prepared from culture supernatants (b) OX8; an anti-rat CD8 antibody (mouse IgG1). The hybridoma producing OX8 was originally obtained from Dr. Alan Williams (Oxford, UK). In some experiments Fab fragments of OX8 was used. The fragments were prepared by papain digestion followed by removal of Fc fragments and any undigested OX8 on protein A (c) MO1, MO2 and MO3; mouse Mabs directed against TLTF. MO1 was prepared as described previously (Bakhiet et al 1993, supra), while MO2 and MO3 were produced recently. Two male DBA/2 mice were immunized in the foot pads with a gel fraction of *T.b. brucei* that showed a high ability to induce MNC to IFN-γ production (Olsson et al 1991, supra; Bakhiet et al 1993, supra). The immunogen and Freund's complete adjuvant (Sigma, St. Louis) was mixed 1:1 and 50 µl of this mixture was injected into each hind foot pad. Eleven days later regional lymph nodes were removed. Suspended lymphocytes from these nodes were hybridized with mouse Sp 2/0 cells as previously described (Holmdahl, R., Olsson, T., Moran, T., Klareskog, L., "In vivo treatment of rats with monoclonal anti-T-cell antibodies. Immunohistochemical and functional analysis in normal rats and experimental allergic neuritis", Scand. J. Immunol. 1985; 22:157–169). Subcloning was done once and hybridomas, whose supernatants inhibited or stimulated TLTF induced IFN-γ production by rat mononuclear cells cultures were selected. Ten hybridomas supernatants significantly inhibited TLTF induced IFN-γ production, while 7 hybridomas exhibited stimulatory effects. One of the inhibitory hybridomas (MO2) and one of the stimulatory hybridomas (MO3) were further propagated and characterized. Both of these hybridomas produced antibodies of the IgG 2b subclass, and were purified on Protein A Sepharose according to standard techniques.

The affinity purified TLTF (Bakhiet et al., 1993, supra) was also used to immunize rabbits to generate immune sera according to standard protocols. The anti-TLTF polyclonal antibody (NR4) from rabbit number 300 was used for immunoblotting and for screening of the trypanosome cDNA library.

Preparation of Mononuclear Cell Suspensions

Mononuclear cells were prepared from rats and mice spleens, and from human peripheral blood. To prepare spleen MNC, animals were sacrificed, the spleens dissected and crushed through a stainless steel meshwork. The cells were washed once in tissue culture medium. The medium consisted of Isocove's modified Dulbecco's medium (Flow lab. Irvine, UK) supplemented with 5% foetal calf serum (GIBCO, Baisley, UK), 1% minimal essential medium (Flow Lab), 2 mM glutamine (Flow Lab), 50 $\mu$g/ml penicillin, and 60 $\mu$l,/ml streptomycin. Erythrocytes in the cell pellets were haemolysed by adding 2 ml cold sterile water for 30 sec followed by addition of 1 ml 2.7% saline. The cells were then washed in medium twice and rediluted to obtain a cell concentration of $5\times10^6$/ml. The cells were then washed twice in medium and rediluted to obtain appropriate cell concentrations (see below). Human peripheral blood cells from healthy donors were obtained by density gradient centrifugation. In some experiments human CD8 and CD4 enriched populations were used. They were isolated by negative selection using Mab coated magnetic beads as described previously (Olsson et al 1993, supra).

Single Cell Assay for IFN-$\gamma$ Secretion.

The method described by Czerkinsky et al 1988 as adapted to rat IFN-$\gamma$ (Mustafa, M. I., Diener, P., Höjeberg, B., Van der Meide, P., and Olsson, T., "T cell immunity and interferon-$\gamma$ secretion during experimental allergic encephalomyelitis in Lewis rats", J. Neuroimmunol. 1991; 31: 165–177) was used to detect IFN-$\gamma$ production by single secretory cells. In principle, nitro-cellulose-bottomed, 96 well microtitre plates (Millipore, Bedford, Mass.) were coated overnight with 15 $\mu$g/ml (100 $\mu$l aliquots) of the mouse monoclonal antirat IFN-$\gamma$ antibody DB1, which crossreacts with mouse IFN-$\gamma$ (Van Der Meide, P. H., Dubbeld, M., Vijverberg, K., Kos, T., Schellekens, H, "The purification and characterization of rat gamma interferon by use of two monoclonal antibodies", J. Gen. Virol. 1986; 67: 1059–1071). DB1 was a generous gift from Dr. Peter Van der Meide, TNO Center, Netherlands. After repeated washings with PBS, 2% bovine serum albumin was applied for 2–4 h, the plates were washed in PBS and aliquots of $5\times10^5$ MNC (200 $\mu$l) were applied in triplicate. Ten $\mu$l aliquots of native TLTF, recombinant material (see below) or Con A as a control were added to different cultures. In some experiments other reagents were added (see below). This was followed by incubation overnight at 37° C. in humidified atmosphere of 7% $CO_2$. Cells were then removed by flicking the plate, followed by repeated washings in PBS. Polyclonal rabbit anti-rat IFN-$\gamma$ (Van der Meide et al 1986, supra), diluted 1/1000, was applied for 4 h. After washing, biotinylated goat anti-rabbit IgG (Vector Lab, Burlingame, Calif.) was applied for 4 h followed by avidine-biotin-peroxidase complex (ABC Vectastain Elite Kit, Vector Lab). Peroxidase staining with 3-amino-9 ethylcarbazole and $H_2O_2$ was performed (Kaplow, L. S: "Substitute of benzidine in myeloperoxidase stains", Am. J. Clin. Pathol. 1974; 63:451). Spots corresponding to cells that had secreted IFN-$\gamma$ were counted in a dissection microscope.

Lymphocyte Proliferation Assay

Aliquots of $5\times10^5$ MNC (200 $\mu$l) were added in triplicate to 96-round-bottomed well microtitre plates (Nunc, Copenhagen, Denmark). The cells were incubated 72 h after addition of 10 $\mu$l aliquots of native TLTF, recombinant material (see below) or Con A as a control. Ten h before harvest 10 $\mu$l aliquots containing 1 $\mu$Ci of [$^3$H]-methylthymidine (specific activity 42 Ci/mmol) (Amersham, Little Chalfont, UK) in saline were added to each well. Cells were harvested onto glass fibre filters with a multiple channel semiautomated harvesting device (Titertek, Skatron AS, Lierbyen, Norway) and thymidine incorporation was measured as counts per minute (CPM) in a liquid betascintillation counter (Mark II, Searle, Analytic, Des Plaines, Ill., USA).

Cell ELISA for TLTF-CD8 Interaction

Hundred $\mu$l aliquots of $10^5$ cells in suspension were added and allowed to dry into wells of polystyrene microtitre plates (Nunc, Copenhagen, Denmark). The plates were washed with PBS, pH 7.4, and wells subjected to 0.5% bovine serum albumin (BSA, Sigma) for 24 h at room temperature. After washing with PBS, 100 $\mu$l aliquot of different dilution or no TLTF were added for 2 h. After washing with PBS, biotinylated MO3 was added, followed by ABC al P. Enzyme substrate solution was added and absorvence measured at 405 nm in a multiscan photometer (Labsystem, Helsinki, Finland).

Antibody Modulation Experiments

Tel $\mu$l aliquots of the IB-4, OX8, MO1, MO2 and MO3 Mabs to obtain final concentration in medium of 5 $\mu$g/ml were added to microtitre plate wells immediately after plating the MNC. Ten $\mu$l aliquots of native TLTF, recombinant material or as control similar volumes of Con A (5 $\mu$g/ml as final concentration in medium; Pharmacia, Uppsala, Sweden) were added. After 24 h of culture the effects on IFN-$\gamma$ secretion and after 72 h the effect on cell proliferation were determined.

Procedure used for Cloning the Gene Encoding TLTF

The gene was cloned from a $\lambda$ZAPII (Stratagene) cDNA library constructed with total RNA isolated from blood stream forms of *Trypanosoma brucei rhodesiense* clone MVAT4 Rx. Host strain cells (bacterial strain) for the Lambda ZAP II Vector (phage) used here was XL1-Blue MRF'. Predigested $\lambda$Zap II/EcoR I/CIAP cloning kit (Stratagene) was used to construct and amplify the Lambda Zap II library according to the instruction manual.

Preparation of Plating Bacteria for Phage Lambda:

Using sterile technique, bacterial host from a single colony was inoculated into NCZYM medium, pH 7.5 (50 ml in 250 ml flask). Maltose in final concentration of 0.2% (0.5 ml of 20% stock ) was added to induce malt operon, which contains the gene lamb for the lambda receptor. The bacteria were allowed to grow overnight with shaking at 30° C. This lower temperature ensures that the cells will not overgrow. After incubation, the cell suspension was poured into centrifuge tubes and spinned in bench Sorvsall for 10 minutes at about 3500 rpm. The supernatant was discarded and the pellet was re-suspended in 20 ml 10 mM $MgSO_4$. Optical density was measured at 600 nm against a blank of 10 mM $MgSO_4$ and adjusted to 2 by adding more $MgSO_4$ or re-pelleting cells and re-suspending them in a smaller volume. The cells were stored in aliquots at 4° C. until use.

Plating Phage:

LB Broth medium supplemented with 1% agar that has been autoclaved was poured into plates placed on flat surface. The surface of the poured plate was flamed to remove any air bubbles. When agar had set, plates were put to dry in 37° C. oven overnight in inverted position. Next day, 80 $\mu$l of plating bacteria was mixed by inversion with 180 $\mu$l phage suspension from different dilutions and incubated at 37° C. for 15–20 minutes. Meanwhile, top agar was melted and dispensed in 8 ml volumes into sterile Falcon tubes, which are then placed in a water bath at 46° C. to equilibrate. Following phage/bacterial incubation, molten top agar was removed from water bath and mixed gently with the diluted phage and host strain using vortex at minimum speed to prevent introducing bubbles. The mixer poured quickly into center of plate in smooth motion and plate was rocked to create an even layer. Plates were left to set for 15 minutes and then incubated overnight at 37° C. in inverted position. After incubation, the number of plaques was counted and the plaque forming units (pfu) was determined per ml concentration of the library based on the dilution.

Immunoscreening:

After titration of the bacteriophage, $2.7 \times 10^4$ pfu were incubated with XL-1 Blue cells to obtain plaques. The plaques were then lifted in doublicate on nitrocellulose filters (Schleicher & Schuell) impregnated with 0.01M IPTG. Filters were blocked in 5% milk at 4° C. overnight to decrease non-specific binding. Immunoscreening was done using as primary antibody the rabbit polyclonal sera, from rabbit number 300, (NR4) directed against the MO1 affinity purified TLTF. The primary antibody was diluted 1:2000, pre-absorbed with E.coli lysate (Bio-Rad) and incubated with the filters for 2 hours at room temperature. Horseradish peroxidase-linked anti-rabbit donkey IgG (Amersham) diluted 1:5000 was applied for 2 hours at room temperature. Positive plaques were detected using ECL chemiluminescent system (Amersham) where 6 potential phages were picked. The phage titer for the six selected phage was amplified and a secondary immunoscreening was done as described above using 100 µl of $10^{-3}$ dilution of each phage elute. After detection by ECL system, phage 1 and 2 were positive; phage 3 was negative and phage 4,5 and 6 were borderline. Three phages from each group were picked and eluted in SM buffer and phage titer from each pick was amplified.

Rescue of Phagemids and Expression of the Protein:

The inserts in each phage were rescued into SOLR cells using the ExAssist™ helper phage (M13) obtained from Stratagene. One clone from each rescue was analyzed further by Western blot. Only one clone (#2.3) had reactive protein, therefore, decided to sequence as TLTF. The nucleotide sequence of #2.3 was determined by using the dedeoxy sequencing method (sequence 2.0 kit, USB). Synthetic oligo primers were used to obtain overlapping sequence. Re-cloning of the gene and different truncated forms was done in the ThioFusion Expression system. Proteins were then purified and examined for TLTF biological activity.

STATISTICS

Mann-Whitney's test was used for statistical significance.

Figure 4A:
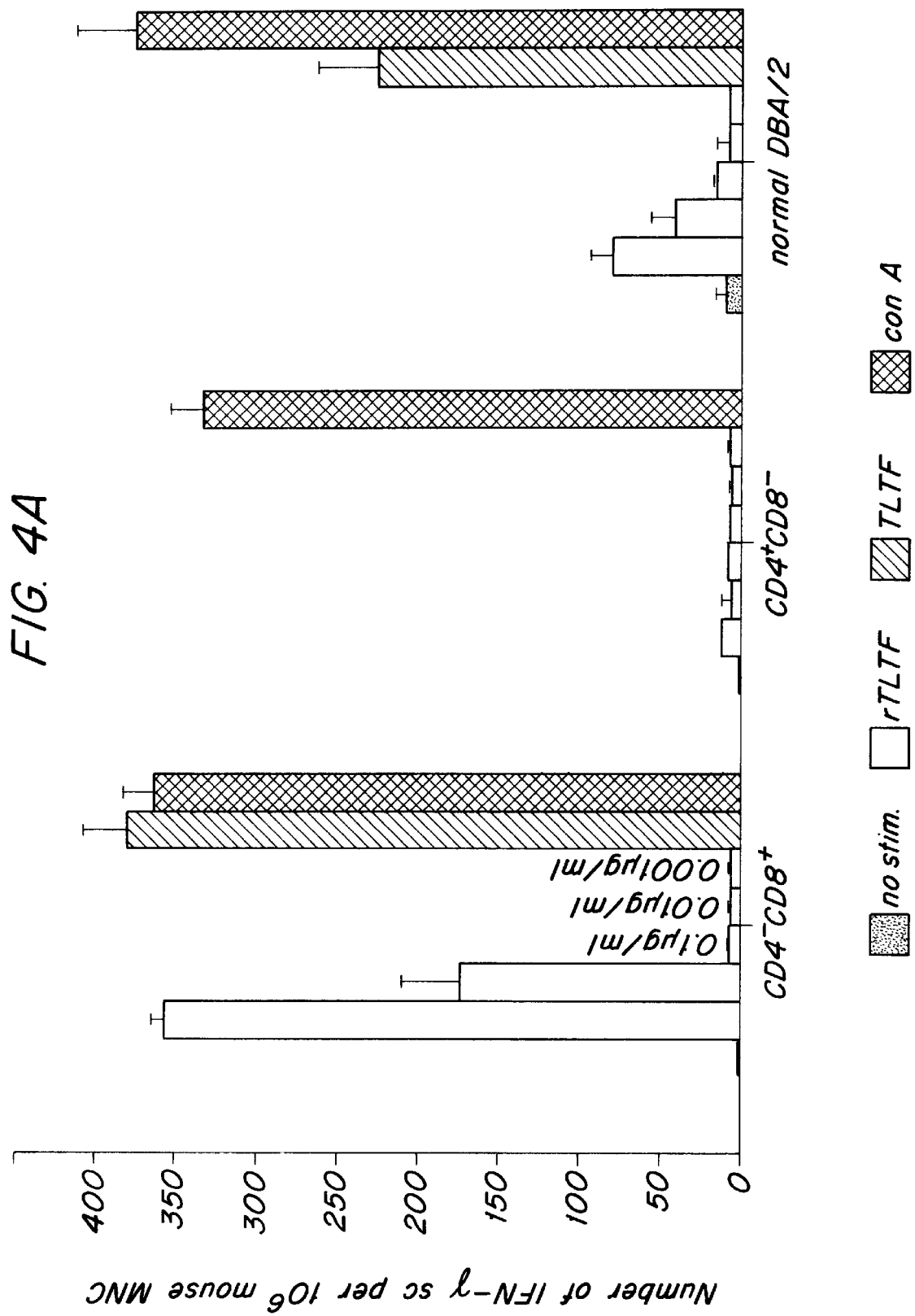
FIG. 4 shows the effects of TLTF and rTLTF on MNC from mice with genomic deletion of CD8+ or CD4+ T cells.

RESULTS cDNA Sequence of the Recombinant TLTF:

The complete cDNA sequence of the recombinant TLTF, clone #2, is shown in FIG. 1A. From 3 reading frames, the 2nd, which is shown, is the longest one and it is open until near the polyA at the 3'end. Supposing that the first MET in this reading frame is a start MET, the deduced protein has 467 amino acids. A geneBank search did not reveal any significant homologies. Using PCR-based approach, 3 truncated forms of the molecule were obtained and overexpressed. Truncated forms of the recombinant protein, disclosed in FIGS. 1A–H, are examined to define the minimum length of the TLTF with retained bioactivity. A 145 amino acids long part of the molecule (#4, which is the shortest part; amino acid 1–145) is still biologically active (FIG. 4B). The translation of the TLTF clone #2 is shown in FIG. 1B. The C terminus of this deduced protein is very hydrophobic, suggesting that the protein is either in a membrane or is secreted. In Western blot analysis of the recombinant *E.coli* extract, using NR4 (TLTF polyvalent antisera), the corresponding fusion protein has the same sized bands as the native TLTF and *T.b. rhodesiense* lysate (not shown).

IFN-γ Production by Rat Splenocytes in Response to rTLTF and MO1 Blocking Effect In the present work we have evaluated IFN-γ production in form of number of cells secreting the cytokine, detected in an antibody capture immunospot assay (FIG. 2). Lymphoid rat MNC cultures were exposed to antibody affinity purified TLTF diluted $10^{-3}$, 1 $\mu$g/ml rTLTF and 1 $\mu$g/ml of an irrelevant oncoserca protein (OV7) that has been cloned and expressed in a similar way to rTLTF. Other cultures were left non-stimulated. Native TLTF and rTLTF induced significant number of cells to produce IFN-γ compared t non-stimulated cells while OV7 did show a significant effect on IFN-γ produced by rat MNC. The monoclonal mouse anti-TLTF (MO1) was incubated at a concentration of 5 $\mu$g/ml with MNC in a set of experiments. This was followed by addition of the 3 proteins to stimulate the cells. MO1 significantly inhibited native TLTF and rTLTF induced IFN-γ production by MNC.

Thus, in FIG. 2, the number of IFN-γ secreting cells determined in the immunospot assay are shown. Normal rat splenocytes suspension was plated at a concentration of $10^6$ MNC per well and cultured for 24 h. Triplicate cultures were exposed to optimal dilutions of native TLTF, rTLTF at a concentration of 1 $\mu$g per ml or OV7 (oncosera protein that has been cloned and expressed in a similar way to rTLTF) at a concentration of 1 $\mu$g per ml. Control cultures received no stimulation. Similar data were obtained on three different occasions. Note the inhibitory effect by anti-TLTF mouse monoclonal antibody (MO1) at a concentration of 5 $\mu$g/ml on both native TLTF and rTLTF when incubated with MNC prior to stimulation. As shown previously (Bakhiet et al., 1993, supra), MO1 did not show any effect when incubated with Con A or with non-stimulated MNC. Bars denote S.D.

Effect of Anti-TLTF Antibodies on RTLTF-induced IFN-γ Production by Human Peripheral Blood Lymphocytes (PBL)

The immunospot assay was also used here to evaluate the action of the recombinant TLTF on human PBL and to study the effects of anti-TLTF monoclonal antibodies in the rTLTF triggering activity. Thus, native TLTF at $10^{-3}$ dilution, lug and 0.1 $\mu$g rTLTF per ml all induced PBL to produce IFN-γ. Both MO1 and MO2 are monoclonal antibodies that showed inhibitory effect on native TLTF-induced IFN-γ production. The 2 monoclonals herein significantly inhibited the triggering effect of rTLTF at a concentration of 0.1 $\mu$g/ml on PBL. Conversely, MO3, a third monoclonal antibody against native TLTF with stimulatory effect, has also exhibited here an enhanced effect on rTLTF-induced IFN-γ production (FIG. 3).

Thus, FIG. 3 shows the monoclonal anti-TLTF antibodies effects on rTLTF triggering of human peripheral blood (PBL). After 24 h of culture the number of IFN-γ secreting cells was measured by the immunospot assay. Immediately before addition of rTLTF, different cultures received mouse monoclonal antibodies (MO1, MO2 or MO3) to reach a final concentration in the medium of 5 $\mu$g/ml. Other cultures received no antibodies. Note that rTLTF induced IFN-γ production by human (PBL) was inhibited by MO1 and MO2, while MO3 enhanced the effect of the rTLTF. Irrelevant antibodies (OX19, W3/13, W3/25, Hy2-15) were previously shown to have no effects (Olsson et al, 1993, supra). Each staple represent data from triplicate or quadruplicate cultures. Bars denote S.D. The experiment was repeated twice with similar results.

Studies on Cells of Mice with CD8-, CD4-genotype and Normal DBA/2

MNC from mutant mice lacking CD8 or CD4 and normal DBA/2 used to study (a) IFN-γ production (b) T cell proliferation and (c) TLTF-CD8 binding. In vitro stimulation of spleen MNC obtained from the 3 mouse strains showed no increased IFN-γ production using native or recombinant TLTF in CD8⁻ mice, while Con-A induced high production of IFN-γ studied in these mice (FIG. 4A). Similar effect was recorded when proliferation assay was used. Thus, native and recombinant TLTF did not trigger MNC from CD8⁻ mice, while Con A showed a high proliferative response in all groups. OV7 was used as a control in this assay and did not exhibit any effect (FIG. 4B). The direct binding of TLTF to CD8 was studied by applying native or rTLTF to mouse CD8⁺CD4⁻ or CD4⁺CD8⁻ mononuclear cell suspensions using cell ELISA. TLTF was allowed to interact with thymocytes from mice with genomic deletions of CD4 or CD8. Thus, binding of TLTF (native and recombinant) was recorded in microtitre plate wells that had been coated with thymocytes containing CD8⁺ cells from the genomically CD4 detected mice, but not in wells that had been coated with thymocytes containing CD4⁺ cells from genomically CD8 deleted mice. A signal above background was obtained with dilution of TLTF down to $10^{-3}$ during exposure to the CD8⁺ containing wells (FIG. 4).

Figure 4C:
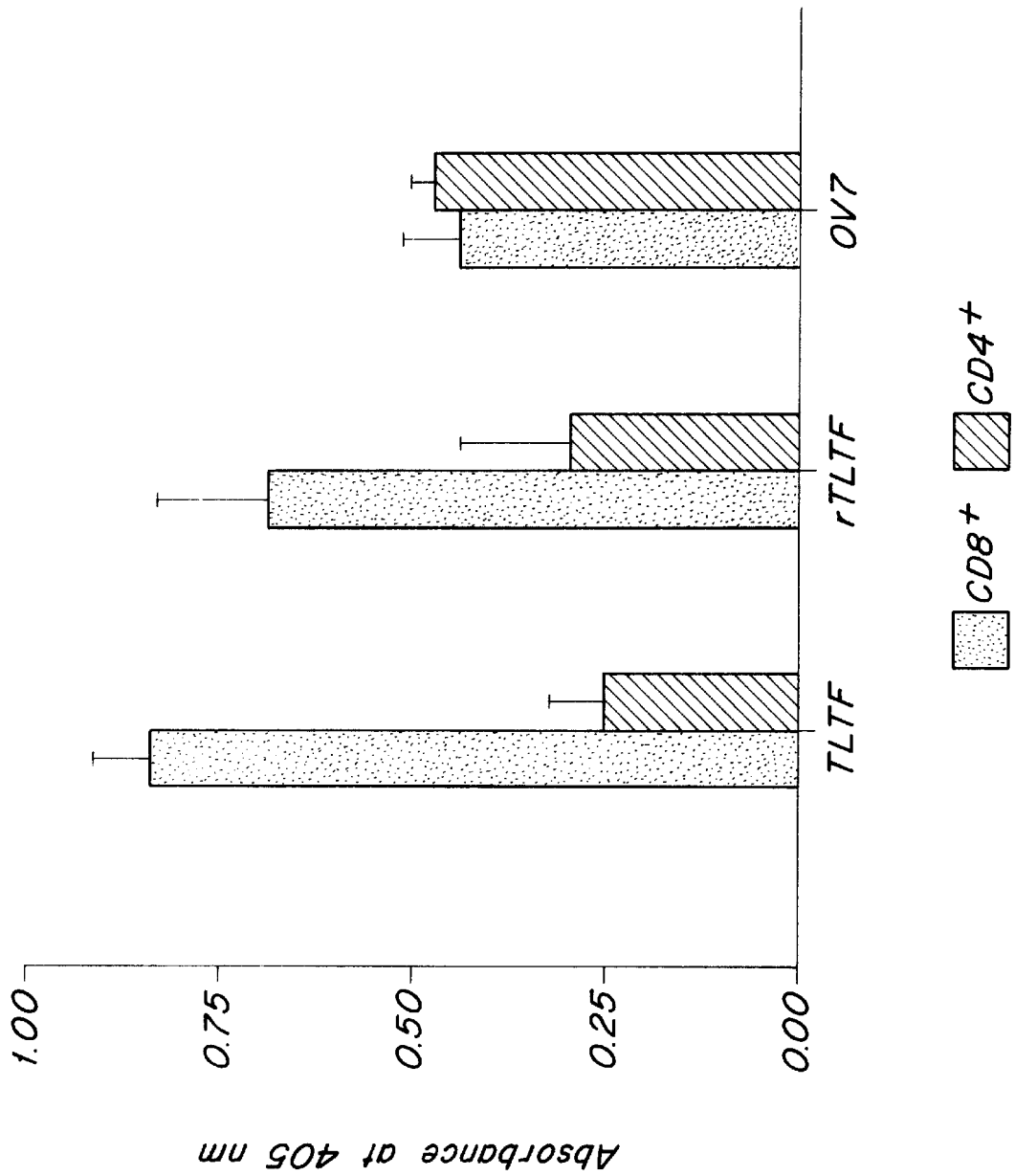

Thus, in FIG. 4, the effects of TLTF and rTLTF on MNC from mice with genomic deletion of CD8⁺ or CD4⁺ T cells are shown. IFN-γ production (number of IFN-γ secreting cells) was measured after 24 h of culture (A), while proliferation as assessed by ³H-thymidine uptake was measured after 72 h. MNC were either stimulated with the whole rTLTF or the shortest truncated form #4 (B). Each staple represent data from triplicate or quadruplicate cultures. Bars denote S.D. The experiment was repeated several times with similar results. (C) Absorbance readings in a cell ELISA to study the TLTF-CD8 binding. Mouse thymocytes from genomically CD4⁻ mice (containing CD8⁺ cells) or CD8⁻ mice (containing CD4⁺ cells) were dried onto plastic of microtitre plate wells. TLTF, rTLTF or OV7 were applied and binding detected by a biotinylated mouse monoclonal anti-TLTF (MO3). Values denote readings from 6–12 wells after subtraction of the background. Bars denote S.D. Note selective binding of TLTF and rTLTF, but not OV7, to wells containing CD8⁺ cells.

rTLTF Immune Sera Blocking Studies on Native TLTF-induced IFN-γ Production

Immune sera from 2 immunised mice with the rTLTF and their preimmune sera were used in blocking experiments to inhibit native TLTF-induced IFN-γ production. The preimmune sera from the 2 mice did not show any effect, while the 2 immune sera significantly inhibited the induction of IFN-γ by TLTF (FIG. 5).

Figure 5:
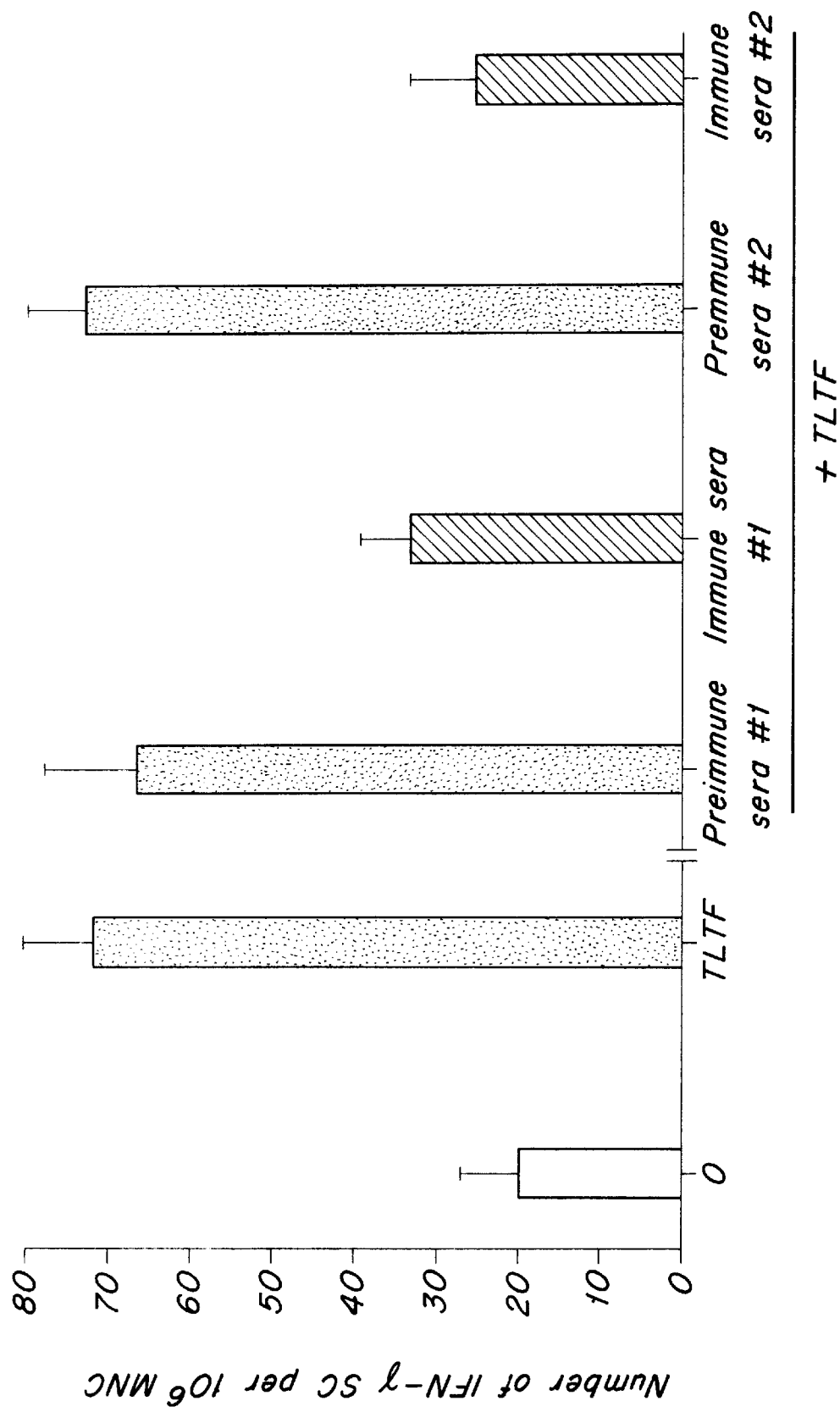
FIG. 5 shows the anti-rTLTF immune sera inhibitory effect on native TLTF-induced IFN-$\gamma$ as measured by the immunospot assay.

Thus, FIG. 5 depicts anti-rTLTF immune sera inhibitory effect on native TLTF-induced IFN-γ as measured by the immuneospot assay. Preimmune sera gave no effect. Each staple denote reading from 8 cultures. Bars denote S.D.

DISCUSSION

Native TLTF is a glycoprotein that was characterized for its main biological activities, which is determined by the ability to bind CD8 molecule and stimulate CD8⁺ cells to produce IFN-γ and to proliferate. Evidence for such a role was previously obtained by studying *T.b. brucei* infection in rats or mice. In the former, CD8⁺ T cells had been depleted in vivo by anti-CD8 antibodies (Bakhiet et al., 1990, supra) or in vitro (Olsson et al., 1991, supra). While in the later, CD8 was genomically deleted (Olsson et al., 1993, supra). Herein, the functional assays used to demonstrate that the cloned material has similar biological activities as the native TLTF are consequently (a) immunospot method for detection of IFN-γ secreting cells by MNC from rats, humans and mice with genomically deleted CD8 or CD4, (b) T cell proliferation technique and (c) CD8 binding assay. *T.b. brucei* triggers a high number of lymphoid MNC to IFN-γ secretion in vitro, while lymphoid cell proliferation as measured by ³H-thymidine uptake is relatively minor (Olsson et al., 1991, supra). However, CD8⁺CD4⁻ MNC showed a more potent proliferative response after triggering with TLTF than normal rat or mouse MNC (data not shown). It is tempting to suggest that this simply is due to a higher proportion of CD8⁺ TLTF responder cells. All above methods showed that rTLTF selectively acts on CD8. CD8 is a heterodimer with 52% amino acid sequence homology between rat and human (Johnson, P., Gagnon, J., Barclay, A. N., and Williams, A. F. (1985), "Purification, chain separation and esquence of the MRC OX-8 antigen, a marker of rat cytotoxic T lymphocytes", EMBO J., 4, 2539–2545). It was suggested that native TLTF may act on interspecies conserved parts of CD8 since it has triggered rat, mouse and human CD8⁺ T cells (Olsson et al., 1993, supra). As native TLTF, rTLTF exhibited same effects on CD8⁺ cells from all those species. This activity is nevertheless either blocked by the anti-TLTF monoclonal antibodies MO1 and MO2 or enhanced by MO3. Also, immune sera against recombinant TLTF inhibited the native TLTF activity. Previously, we estmiated that roughly one out of 10–20 CD8⁺ T cells were triggered by native TLTF (Olsson et al., 1993, supra). Furthermore, native TLTF is active at very low dilution where no measurable protein could be detected. However, rTLTF was active to a dilution of 0.1 μg per ml. This difference in the concentration of the protein required for biological activity may be related to the absence of carbohydrate molecules in the recombinant protein since it is expressed in *E.coli*. Carbohydrate was shown to be of importance for dynamic biological activity (Bakhiet et al., 1993, supra). Moreover, the recombinant material is insoluble in water, which might also be related to the absence of the carbohydrate. Thereby, methods for purification by elution from gel may affect its activity. In order to overcome this problem expression in other systems, such as mammalian cells, should be tried.

One key approach for protection from African trypanosomiasis is to target invariable molecules that are interacting with the host defens system. Recently, Ziegelbauer K and Overath P., "Identification of invariant surface flycoproteins in the bloodstream stage of *Trypanosoma brucei*, J. Biol. Chem. 1992; 267:10791–10796) described a class of invariable surface molecules, two of them were isolated and the corresponding genes cloned (Ziegelbauer K, Multhaup G and Overath P., "Molecular characterization of the two invariant surface glycoproteins specific for the bloodstream stage of *Trypanosoma brucei*., J. Biol. Chem. 1992; 267:10797–10803). They are inserted in the membrane between the VSG molecules and covered by them. Therefore, they are not accessible to antibodies. In passive immunotherapy, injection of the anti-TLTF monoclonal antibody (MO1) into *T.b. brucei* infected animals resulted in lower parasitemia and prolonged survival. This was of strong indication for cloning the TLTF to be used in an active immunotherapy. This work gives evidence for a correct clone for the native TLTF. The recombinant TLTF will hence be used for vaccination attempts and also will be explored in a broader sense in Biomedicine such as in CD8 targeted immune interventions.

CONCLUSION

Trypanosome-derived lymphocyte triggering factor (TLTF) is a glycoprotein component secreted by *Trypano-* soma brucei (T.b.) and binds to CD8 molecule. TLTF-CD8 binding activates CD8+ T cells to produce IFN-γ and to proliferate. IFN-γ in turn stimulates parasite growth. In this study, the gene coding for the TLTF has been isolated. The nucleotide sequence indicates no relationship to other genes. The deduced protein has 467 amino acids with a very hydrophobic T-terminus, suggesting that the protein is either in a membrane or is secreted. Shorter truncated forms of the recombinant protein (rTLTF) were obtained and examined for biological activities that are characteristic for native TLTF. Thus, rTLTF and its truncated forms were evaluated for their ability to trigger MNC from rats, humans and mice—with genomically deleted CD8 or CD4—to produce IFN-γ and to proliferate. CD8 binding studies revealed that rTLTF selectively binds to the CD8+ cells and trigger these cells to IFN-γ production and proliferation. The data presented here strongly indicate that the cloned gene is coding for the native TLTF and thereby can be used in further immunobiological studies and in CD8 targeted immune interventions.

We claim:

1. A truncated lymphocyte stimulating factor polypeptide that, upon in vivo administration in a mammal, stimulates CD8+ T-cells to release gamma interferon, thereby resulting in immunosuppression or immunostimulation, wherein said polypeptide consists of amino acids 1 to 467 of SEQ. ID. NO: 17 or a fragment of amino acids 1 to 467 of SEQ. ID. NO. 17 possessing said in vivo activity.

2. A truncated lymphocyte stimulating factor polypeptide according to claim 1, which consists of amino acids 1 to 467 of SEQ. ID. NO. 17.

3. The truncated lymphocyte stimulating factor polypeptide according to claim 1, wherein said fragment comprises at least 150 contiguous amino acids of SEQ. ID. NO. 17.

4. A truncated lymphocyte stimulating factor polypeptide according to claim 1, which comprises at least 100 contiguous amino acids of SEQ. ID. NO. 17.

5. A truncated lymphocyte stimulating factor polypeptide according to claim 1, which comprises at least 120 contiguous amino acids of SEQ. ID. NO. 17.

6. A truncated lymphocyte stimulating factor polypeptide that, upon in vivo administration in a mammal, stimulates CD8+ T-cells to release gamma interferon, thereby resulting in immunosuppression or immunostimulation, wherein said polypeptide consists of amino acids 1 to 311 of SEQ. ID. NO. 19 or a fragment of amino acids 1 to 311 of SEQ. ID. NO. 19 which, upon in vivo administration in a mammal, stimulates CD8+ T-cells to release gamma interferon, thereby resulting in immunosuppression or immunostimulation.

7. A truncated lymphocyte stimulating factor according to claim 6, which consists of amino acids 1 to 311 of SEQ. ID. NO. 19.

8. A truncated lymphocyte stimulating factor that, upon in vivo administration in a mammal, stimulates CD8+ T-cells to release gamma interferon, thereby resulting in immunosuppression or immunostimulation which consists of amino acids 1 to 452 of SEQ. ID. NO. 18 or a fragment of amino acids 1 to 452 of SEQ. ID. NO. 18, which, upon in vivo administration in a mammal, stimulates CD8+ T-cells to release gamma interferon, thereby resulting in immunosuppression or immunostimulation.

9. A truncated lymphocyte stimulating factor according to claim 8, which consists of amino acids 1 to 452 of SEQ. ID. NO. 18.

10. A truncated lymphocyte stimulating factor polypeptide that, upon in vivo administration in a mammal, stimulates CD8+ T-cells to release gamma interferon, thereby resulting in immunosuppression or immunostimulation, wherein said polypeptide consists of amino acids 1 to 145 of SEQ. ID. NO. 20 or a fragment of amino acids 1 to 145 of SEQ. ID. NO. 20 possessing said in vivo activity.

11. A truncated lymphocyte stimulating factor polypeptide according to claim 10, wherein the polypeptide consists of amino acids 1 to 145 of said SEQ. ID. NO. 20.

12. A pharmaceutical composition containing a polypeptide according to claim 1 and a pharmaceutically acceptable carrier.

13. A pharmaceutical composition containing a polypeptide according to claim 2 and a pharmaceutically acceptable carrier.

14. A pharmaceutical composition containing a polypeptide according to claim 3 and a pharmaceutically acceptable carrier.

15. A pharmaceutical composition containing a polypeptide according to claim 4 and a pharmaceutically acceptable carrier.

16. A pharmaceutical composition containing a polypeptide according to claim 5 and a pharmaceutically acceptable carrier.

17. A pharmaceutical composition containing a polypeptide according to claim 6 and a pharmaceutically acceptable carrier.

18. A pharmaceutical composition containing a polypeptide according to claim 7 and a pharmaceutically acceptable carrier.

19. A pharmaceutical composition containing a polypeptide according to claim 8 and a pharmaceutically acceptable carrier.

20. A pharmaceutical composition containing a polypeptide according to claim 9 and a pharmaceutically acceptable carrier.

21. A pharmaceutical composition containing a polypeptide according to claim 10 and a pharmaceutically acceptable carrier.

22. A pharmaceutical composition containing a polypeptide according to claim 11 and a pharmaceutically acceptable carrier.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 1750 base pairs
        ( B ) TYPE: nucleic acid
        ( C ) STRANDEDNESS: unknown
        ( D ) TOPOLOGY: unknown ( i i ) MOLECULE TYPE: cDNA ( v i ) ORIGINAL SOURCE:
        ( A ) ORGANISM: TLTF ( x i ) SEQUENCE DESCRIPTION: SEQ ID NO:1:

```
TATATTGACT  GCATCGTGGC  GTACCCCGTA  GGCTCTTCTC  GTTTTTGAAT  GTCACCACGG       60
ACCGGTGCTG  AGCGCGGAGG  AAGGAGAAAG  TCAGTCAAGG  CCCCGCCACC  AGTTGATCCT      120
CTAGTGGAGC  TCACAACTTT  AGAATCGGTT  CATGACGCGT  TGGCGAAGGC  CGAGCGACTT      180
CGGAACTACT  TCCAGGTAGA  GCGTGACAAG  GTGAATGACT  TCTGGACGAT  TACAAAGGGG      240
GAGGTGGAGA  CTTATCGCAA  TCGGCTGTTC  AATGCGGAGG  CGAGCATTGA  AGAACTGGAG      300
CGGTCACACC  AGGTAGAGAT  GAAGGTATAC  AAGCAGAGGG  TGCGTCACCT  CATCTATGAG      360
CGGAAGAAGA  AGGCGCAGGC  GTGCCAGGAT  GAAAGTCACC  GTCTGCTTCG  CGAGGCGGAA      420
GACCGGCACC  TCCAGCGCAT  GAATGAGATA  CAGGCTAAGC  TCCAACAGCA  AGACCAGCAG      480
CTCCGGGCAG  CAGCGGCTGA  CCATGAAATG  AACGTGTACG  AGAAGCGCGA  TTCGCACAGC      540
TACATGGTAA  CCGTTACAAA  AACACAGAGT  CATGAAAAGG  AGCTCGCGCG  ACTGCAGGTA      600
TCCTGTGAGG  CCAAGTTAAA  AGTGTTGCGG  GATGAACTGG  AGTTAAGACG  CCGTCGCCAG      660
ATTCATGAGA  TTGAAGAAAG  AAAGAATGAG  CACATAAACG  CCCTCATTAA  GCAGCATGAA      720
GAGAAATTTC  ATGAAATGAA  GACATACTAC  AACCAAATAA  CCACAAATAA  CCTAGAAATC      780
ATTCATTCCT  TAAAGGAAGA  AATAGCGCAG  ATGAAGCAGA  ACGACGAGCA  TAATGAGACT      840
TTAATGTATG  ATATTGATCG  GGAGAATCAA  AATCTTGTTG  CACCGTTAGA  AGAAGCTCAG      900
CGTGAGGTTG  CGGAGCTGCA  GCAGAAACGG  AAGCAGAATG  AACAGAACAA  GCGGGGTCTC      960
GAGGTCACTC  GTGTTAAGTT  AAGGTCGTTG  CGTGAGGAGA  TTCGCCGACA  GCGTGAAGAA     1020
CATCAGGCCT  TGGAGGAGCG  TTACGCCTGC  GTGCACCGGG  AGCGCGAGGA  GCTCAAGGGG     1080
AAGTTTGAGT  CCGCGCTCCG  GCAAGCGGTG  ATGGTAGTCG  AGGAGCGCAA  TGAGGTTCTC     1140
CAGCAAAAGC  TTATCGAGTC  TCACGCTCTT  GTAGAGGAAA  GGGATGTACA  ACTTGAAGGT     1200
GTTTTGCGCG  CCATGAACCT  CGAACCAAAG  ACGCTGGAAC  TCATCGCGAC  TGAGGTCGAC     1260
GAATGGCTTC  AACGAAAAAA  TCAACTGATA  AAAGACTTAC  ACTTTGAGCT  TAAGAAAGGA     1320
```

-continued

```
GAAAAGTTGT ACAGCGCGAC GTTGCTCGAG ATGGAGAGCG TTGCCAGACG GCTAACATTG   1380

CTTCACTGCC ACGTAGCAAC TTTGAGTAGG TGTTGTGGTT CACACGTTGG TTGTTCCAAG   1440

TTACGGCTTT GTTGCAGCTC GCATTCGGCC GTGGGCGTGG TGGGCTGTTT TTTTTTTTCT   1500

TCTGTCCTGT TGCCTCTTTC CCCTTTCTAG TGGGCCACTG CGCTTCCTAT GGACCTGTGA   1560

ATGTAGAACT ACGCGTCACA CGCCTTGGTA TGTATGTTGT TACGTGCCGG ATATAGAGAC   1620

AGTTGCTGCT GCGACGAGCG TCGTTGTGAG ACGCGTGAGT GATTGCGAGG CGAAACCTAT   1680

AAAGATTGAG GCCGGTTATC ATTGTAACCT CACTTTATTG TCATTTCACT AAAAAAAAAA   1740

AAAAAAAAAA                                                          1750
```

(2) INFORMATION FOR SEQ ID NO:2:

(i) SEQUENCE CHARACTERISTICS:
        (A) LENGTH: 45 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: TLTF (ix) FEATURE:
        (A) NAME/KEY: CDS
        (B) LOCATION: 1..45

(xi) SEQUENCE DESCRIPTION: SEQ ID NO:2:

```
TAT ATT GAC TGC ATC GTG GCG TAC CCC GTA GGC TCT TCT CGT TTT         45
Tyr Ile Asp Cys Ile Val Ala Tyr Pro Val Gly Ser Ser Arg Phe
 1               5                  10                  15
```

(2) INFORMATION FOR SEQ ID NO:3:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:3:

```
Tyr Ile Asp Cys Ile Val Ala Tyr Pro Val Gly Ser Ser Arg Phe
 1               5                  10                  15
```

(2) INFORMATION FOR SEQ ID NO:4:

(i) SEQUENCE CHARACTERISTICS:
        (A) LENGTH: 1479 base pairs
        (B) TYPE: nucleic acid
        (C) STRANDEDNESS: unknown
        (D) TOPOLOGY: linear (ii) MOLECULE TYPE: cDNA (vi) ORIGINAL SOURCE:
        (A) ORGANISM: TLTF (ix) FEATURE:
        (A) NAME/KEY: CDS
        (B) LOCATION: 1..1479

(xi) SEQUENCE DESCRIPTION: SEQ ID NO:4:

```
ATG TCA CCA CGG ACC GGT GCT GAG CGC GGA GGA AGG AGA AAG TCA GTC    48
Met Ser Pro Arg Thr Gly Ala Glu Arg Gly Gly Arg Arg Lys Ser Val
              20                  25                  30

AAG GCC CCG CCA CCA GTT GAT CCT CTA GTG GAG CTC ACA ACT TTA GAA    96
```

-continued

| | | | | | | | | | | | | | | | |
|---|---|---|---|---|---|---|---|---|---|---|---|---|---|---|---|
| Lys | Ala | Pro | Pro<br>35 | Pro | Val | Asp | Pro<br>40 | Leu | Val | Glu | Leu | Thr<br>45 | Thr | Leu | Glu |

| TCG | GTT | CAT | GAC | GCG | TTG | GCG | AAG | GCC | GAG | CGA | CTT | CGG | AAC | TAC | TTC | 144 |
|---|---|---|---|---|---|---|---|---|---|---|---|---|---|---|---|---|
| Ser | Val | His<br>50 | Asp | Ala | Leu | Ala | Lys<br>55 | Ala | Glu | Arg | Leu | Arg<br>60 | Asn | Tyr | Phe | |

| CAG | GTA | GAG | CGT | GAC | AAG | GTG | AAT | GAC | TTC | TGG | ACG | ATT | ACA | AAG | GGG | 192 |
|---|---|---|---|---|---|---|---|---|---|---|---|---|---|---|---|---|
| Gln | Val<br>65 | Glu | Arg | Asp | Lys | Val<br>70 | Asn | Asp | Phe | Trp | Thr<br>75 | Ile | Thr | Lys | Gly | |

| GAG | GTG | GAG | ACT | TAT | CGC | AAT | CGG | CTG | TTC | AAT | GCG | GAG | GCG | AGC | ATT | 240 |
|---|---|---|---|---|---|---|---|---|---|---|---|---|---|---|---|---|
| Glu<br>80 | Val | Glu | Thr | Tyr | Arg<br>85 | Asn | Arg | Leu | Phe | Asn<br>90 | Ala | Glu | Ala | Ser | Ile<br>95 | |

| GAA | GAA | CTG | GAG | CGG | TCA | CAC | CAG | GTA | GAG | ATG | AAG | GTA | TAC | AAG | CAG | 288 |
|---|---|---|---|---|---|---|---|---|---|---|---|---|---|---|---|---|
| Glu | Glu | Leu | Glu | Arg<br>100 | Ser | His | Gln | Val | Glu<br>105 | Met | Lys | Val | Tyr | Lys<br>110 | Gln | |

| AGG | GTG | CGT | CAC | CTC | ATC | TAT | GAG | CGG | AAG | AAG | AAG | GCG | CAG | GCG | TGC | 336 |
|---|---|---|---|---|---|---|---|---|---|---|---|---|---|---|---|---|
| Arg | Val | Arg | His<br>115 | Leu | Ile | Tyr | Glu | Arg<br>120 | Lys | Lys | Lys | Ala | Gln<br>125 | Ala | Cys | |

| CAG | GAT | GAA | AGT | CAC | CGT | CTG | CTT | CGC | GAG | GCG | GAA | GAC | CGG | CAC | CTC | 384 |
|---|---|---|---|---|---|---|---|---|---|---|---|---|---|---|---|---|
| Gln | Asp | Glu | Ser<br>130 | His | Arg | Leu | Leu | Arg<br>135 | Glu | Ala | Glu | Asp | Arg<br>140 | His | Leu | |

| CAG | CGC | ATG | AAT | GAG | ATA | CAG | GCT | AAG | CTC | CAA | CAG | CAA | GAC | CAG | CAG | 432 |
|---|---|---|---|---|---|---|---|---|---|---|---|---|---|---|---|---|
| Gln | Arg<br>145 | Met | Asn | Glu | Ile | Gln<br>150 | Ala | Lys | Leu | Gln | Gln<br>155 | Gln | Asp | Gln | Gln | |

| CTC | CGG | GCA | GCA | GCG | GCT | GAC | CAT | GAA | ATG | AAC | GTG | TAC | GAG | AAG | CGC | 480 |
|---|---|---|---|---|---|---|---|---|---|---|---|---|---|---|---|---|
| Leu<br>160 | Arg | Ala | Ala | Ala | Ala<br>165 | Asp | His | Glu | Met | Asn<br>170 | Val | Tyr | Glu | Lys | Arg<br>175 | |

| GAT | TCG | CAC | AGC | TAC | ATG | GTA | ACC | GTT | ACA | AAA | ACA | CAG | AGT | CAT | GAA | 528 |
|---|---|---|---|---|---|---|---|---|---|---|---|---|---|---|---|---|
| Asp | Ser | His | Ser | Tyr<br>180 | Met | Val | Thr | Val | Thr<br>185 | Lys | Thr | Gln | Ser | His<br>190 | Glu | |

| AAG | GAG | CTC | GCG | CGA | CTG | CAG | GTA | TCC | TGT | GAG | GCC | AAG | TTA | AAA | GTG | 576 |
|---|---|---|---|---|---|---|---|---|---|---|---|---|---|---|---|---|
| Lys | Glu | Leu | Ala<br>195 | Arg | Leu | Gln | Val | Ser<br>200 | Cys | Glu | Ala | Lys | Leu<br>205 | Lys | Val | |

| TTG | CGG | GAT | GAA | CTG | GAG | TTA | AGA | CGC | CGT | CGC | CAG | ATT | CAT | GAG | ATT | 624 |
|---|---|---|---|---|---|---|---|---|---|---|---|---|---|---|---|---|
| Leu | Arg | Asp<br>210 | Glu | Leu | Glu | Leu | Arg<br>215 | Arg | Arg | Arg | Gln | Ile<br>220 | His | Glu | Ile | |

| GAA | GAA | AGA | AAG | AAT | GAG | CAC | ATA | AAC | GCC | CTC | ATT | AAG | CAG | CAT | GAA | 672 |
|---|---|---|---|---|---|---|---|---|---|---|---|---|---|---|---|---|
| Glu | Glu | Arg | Lys<br>225 | Asn | Glu | His | Ile | Asn<br>230 | Ala | Leu | Ile | Lys | Gln<br>235 | His | Glu | |

| GAG | AAA | TTT | CAT | GAA | ATG | AAG | ACA | TAC | TAC | AAC | CAA | ATA | ACC | ACA | AAT | 720 |
|---|---|---|---|---|---|---|---|---|---|---|---|---|---|---|---|---|
| Glu<br>240 | Lys | Phe | His | Glu | Met<br>245 | Lys | Thr | Tyr | Tyr | Asn<br>250 | Gln | Ile | Thr | Thr | Asn<br>255 | |

| AAC | CTA | GAA | ATC | ATT | CAT | TCC | TTA | AAG | GAA | GAA | ATA | GCG | CAG | ATG | AAG | 768 |
|---|---|---|---|---|---|---|---|---|---|---|---|---|---|---|---|---|
| Asn | Leu | Glu | Ile | Ile | His<br>260 | Ser | Leu | Lys | Glu | Glu<br>265 | Ile | Ala | Gln | Met | Lys<br>270 | |

| CAG | AAC | GAC | GAG | CAT | AAT | GAG | ACT | TTA | ATG | TAT | GAT | ATT | GAT | CGG | GAG | 816 |
|---|---|---|---|---|---|---|---|---|---|---|---|---|---|---|---|---|
| Gln | Asn | Asp | Glu | His<br>275 | Asn | Glu | Thr | Leu | Met<br>280 | Tyr | Asp | Ile | Asp | Arg<br>285 | Glu | |

| AAT | CAA | AAT | CTT | GTT | GCA | CCG | TTA | GAA | GAA | GCT | CAG | CGT | GAG | GTT | GCG | 864 |
|---|---|---|---|---|---|---|---|---|---|---|---|---|---|---|---|---|
| Asn | Gln | Asn<br>290 | Leu | Val | Ala | Pro | Leu<br>295 | Glu | Glu | Ala | Gln | Arg<br>300 | Glu | Val | Ala | |

| GAG | CTG | CAG | CAG | AAA | CGG | AAG | CAG | AAT | GAA | CAG | AAC | AAG | CGG | GGT | CTC | 912 |
|---|---|---|---|---|---|---|---|---|---|---|---|---|---|---|---|---|
| Glu | Leu | Gln | Gln<br>305 | Lys | Arg | Lys | Gln | Asn<br>310 | Glu | Gln | Asn | Lys | Arg<br>315 | Gly | Leu | |

| GAG | GTC | ACT | CGT | GTT | AAG | TTA | AGG | TCG | TTG | CGT | GAG | GAG | ATT | CGC | CGA | 960 |
|---|---|---|---|---|---|---|---|---|---|---|---|---|---|---|---|---|
| Glu<br>320 | Val | Thr | Arg | Val | Lys<br>325 | Leu | Arg | Ser | Leu | Arg<br>330 | Glu | Glu | Ile | Arg | Arg<br>335 | |

| CAG | CGT | GAA | GAA | CAT | CAG | GCC | TTG | GAG | GAG | CGT | TAC | GCC | TGC | GTG | CAC | 1008 |
|---|---|---|---|---|---|---|---|---|---|---|---|---|---|---|---|---|
| Gln | Arg | Glu | Glu | His<br>340 | Gln | Ala | Leu | Glu<br>345 | Glu | Arg | Tyr | Ala | Cys<br>350 | Val | His | |

| CGG | GAG | CGC | GAG | GAG | CTC | AAG | GGG | AAG | TTT | GAG | TCC | GCG | CTC | CGG | CAA | 1056 |

-continued

```
Arg  Glu  Arg  Glu  Glu  Leu  Lys  Gly  Lys  Phe  Glu  Ser  Ala  Leu  Arg  Gln
               355                      360                      365

GCG  GTG  ATG  GTA  GTC  GAG  GAG  CGC  AAT  GAG  GTT  CTC  CAG  CAA  AAG  CTT        1104
Ala  Val  Met  Val  Val  Glu  Glu  Arg  Asn  Glu  Val  Leu  Gln  Gln  Lys  Leu
          370                      375                      380

ATC  GAG  TCT  CAC  GCT  CTT  GTA  GAG  GAA  AGG  GAT  GTA  CAA  CTT  GAA  GGT        1152
Ile  Glu  Ser  His  Ala  Leu  Val  Glu  Glu  Arg  Asp  Val  Gln  Leu  Glu  Gly
     385                      390                      395

GTT  TTG  CGC  GCC  ATG  AAC  CTC  GAA  CCA  AAG  ACG  CTG  GAA  CTC  ATC  GCG        1200
Val  Leu  Arg  Ala  Met  Asn  Leu  Glu  Pro  Lys  Thr  Leu  Glu  Leu  Ile  Ala
400                      405                      410                      415

ACT  GAG  GTC  GAC  GAA  TGG  CTT  CAA  CGA  AAA  AAT  CAA  CTG  ATA  AAA  GAC        1248
Thr  Glu  Val  Asp  Glu  Trp  Leu  Gln  Arg  Lys  Asn  Gln  Leu  Ile  Lys  Asp
                    420                      425                      430

TTA  CAC  TTT  GAG  CTT  AAG  AAA  GGA  GAA  AAG  TTG  TAC  AGC  GCG  ACG  TTG        1296
Leu  His  Phe  Glu  Leu  Lys  Lys  Gly  Glu  Lys  Leu  Tyr  Ser  Ala  Thr  Leu
               435                      440                      445

CTC  GAG  ATG  GAG  AGC  GTT  GCC  AGA  CGG  CTA  ACA  TTG  CTT  CAC  TGC  CAC        1344
Leu  Glu  Met  Glu  Ser  Val  Ala  Arg  Arg  Leu  Thr  Leu  Leu  His  Cys  His
          450                      455                      460

GTA  GCA  ACT  TTG  AGT  AGG  TGT  TGT  GGT  TCA  CAC  GTT  GGT  TGT  TCC  AAG        1392
Val  Ala  Thr  Leu  Ser  Arg  Cys  Cys  Gly  Ser  His  Val  Gly  Cys  Ser  Lys
     465                      470                      475

TTA  CGG  CTT  TGT  TGC  AGC  TCG  CAT  TCG  GCC  GTG  GGC  GTG  GTG  GGC  TGT        1440
Leu  Arg  Leu  Cys  Cys  Ser  Ser  His  Ser  Ala  Val  Gly  Val  Val  Gly  Cys
480                      485                      490                      495

TTT  TTT  TTT  TCT  TCT  GTC  CTG  TTG  CCT  CTT  TCC  CCT  TTC                       1479
Phe  Phe  Phe  Ser  Ser  Val  Leu  Leu  Pro  Leu  Ser  Pro  Phe
                    500                      505
```

( 2 ) INFORMATION FOR SEQ ID NO:5:

( i ) SEQUENCE CHARACTERISTICS:
        ( A ) LENGTH: 493 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met  Ser  Pro  Arg  Thr  Gly  Ala  Glu  Arg  Gly  Gly  Arg  Arg  Lys  Ser  Val
 1                  5                      10                      15

Lys  Ala  Pro  Pro  Pro  Val  Asp  Pro  Leu  Val  Glu  Leu  Thr  Thr  Leu  Glu
               20                      25                      30

Ser  Val  His  Asp  Ala  Leu  Ala  Lys  Ala  Glu  Arg  Leu  Arg  Asn  Tyr  Phe
          35                      40                      45

Gln  Val  Glu  Arg  Asp  Lys  Val  Asn  Asp  Phe  Trp  Thr  Ile  Thr  Lys  Gly
     50                      55                      60

Glu  Val  Glu  Thr  Tyr  Arg  Asn  Arg  Leu  Phe  Asn  Ala  Glu  Ala  Ser  Ile
 65                      70                      75                      80

Glu  Glu  Leu  Glu  Arg  Ser  His  Gln  Val  Glu  Met  Lys  Val  Tyr  Lys  Gln
               85                      90                      95

Arg  Val  Arg  His  Leu  Ile  Tyr  Glu  Arg  Lys  Lys  Lys  Ala  Gln  Ala  Cys
          100                     105                     110

Gln  Asp  Glu  Ser  His  Arg  Leu  Leu  Arg  Glu  Ala  Glu  Asp  Arg  His  Leu
     115                     120                     125

Gln  Arg  Met  Asn  Glu  Ile  Gln  Ala  Lys  Leu  Gln  Gln  Gln  Asp  Gln  Gln
     130                     135                     140

Leu  Arg  Ala  Ala  Ala  Ala  Asp  His  Glu  Met  Asn  Val  Tyr  Glu  Lys  Arg
145                     150                     155                     160
```

Asp Ser His Ser Tyr Met Val Thr Val Thr Lys Thr Gln Ser His Glu
                165             170             175

Lys Glu Leu Ala Arg Leu Gln Val Ser Cys Glu Ala Lys Leu Lys Val
            180             185             190

Leu Arg Asp Glu Leu Glu Leu Arg Arg Arg Gln Ile His Glu Ile
        195             200             205

Glu Glu Arg Lys Asn Glu His Ile Asn Ala Leu Ile Lys Gln His Glu
    210             215             220

Glu Lys Phe His Glu Met Lys Thr Tyr Tyr Asn Gln Ile Thr Thr Asn
225             230             235             240

Asn Leu Glu Ile Ile His Ser Leu Lys Glu Glu Ile Ala Gln Met Lys
            245             250             255

Gln Asn Asp Glu His Asn Glu Thr Leu Met Tyr Asp Ile Asp Arg Glu
        260             265             270

Asn Gln Asn Leu Val Ala Pro Leu Glu Glu Ala Gln Arg Glu Val Ala
    275             280             285

Glu Leu Gln Gln Lys Arg Lys Gln Asn Glu Gln Asn Lys Arg Gly Leu
290             295             300

Glu Val Thr Arg Val Lys Leu Arg Ser Leu Arg Glu Glu Ile Arg Arg
305             310             315             320

Gln Arg Glu Glu His Gln Ala Leu Glu Glu Arg Tyr Ala Cys Val His
            325             330             335

Arg Glu Arg Glu Glu Leu Lys Gly Lys Phe Glu Ser Ala Leu Arg Gln
        340             345             350

Ala Val Met Val Val Glu Glu Arg Asn Glu Val Leu Gln Gln Lys Leu
    355             360             365

Ile Glu Ser His Ala Leu Val Glu Glu Arg Asp Val Gln Leu Glu Gly
370             375             380

Val Leu Arg Ala Met Asn Leu Glu Pro Lys Thr Leu Glu Leu Ile Ala
385             390             395             400

Thr Glu Val Asp Glu Trp Leu Gln Arg Lys Asn Gln Leu Ile Lys Asp
            405             410             415

Leu His Phe Glu Leu Lys Lys Gly Glu Lys Leu Tyr Ser Ala Thr Leu
        420             425             430

Leu Glu Met Glu Ser Val Ala Arg Arg Leu Thr Leu Leu His Cys His
    435             440             445

Val Ala Thr Leu Ser Arg Cys Cys Gly Ser His Val Gly Cys Ser Lys
    450             455             460

Leu Arg Leu Cys Cys Ser Ser His Ser Ala Val Gly Val Val Gly Cys
465             470             475             480

Phe Phe Phe Ser Ser Val Leu Leu Pro Leu Ser Pro Phe
            485             490

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: unknown
        ( D ) TOPOLOGY: linear ( i i ) MOLECULE TYPE: cDNA ( v i ) ORIGINAL SOURCE:
        ( A ) ORGANISM: TLTF ( i x ) FEATURE:
        ( A ) NAME/KEY: CDS (B) LOCATION: 1..27

(xi) SEQUENCE DESCRIPTION: SEQ ID NO:6:

| TGG | GCC | ACT | GCG | CTT | CCT | ATG | GAC | CTG | 27 |
|-----|-----|-----|-----|-----|-----|-----|-----|-----|----|
| Trp | Ala | Thr | Ala | Leu | Pro | Met | Asp | Leu |    |
| 495 |     |     |     |     | 500 |     |     |     |    |

(2) INFORMATION FOR SEQ ID NO:7:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:7:

Trp Ala Thr Ala Leu Pro Met Asp Leu
 1           5

(2) INFORMATION FOR SEQ ID NO:8:

(i) SEQUENCE CHARACTERISTICS:
        (A) LENGTH: 93 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: TLTF (ix) FEATURE:
        (A) NAME/KEY: CDS
        (B) LOCATION: 1..93

(xi) SEQUENCE DESCRIPTION: SEQ ID NO:8:

| AAC | TAC | GCG | TCA | CAC | GCC | TTG | GTA | TGT | ATG | TTG | TTA | CGT | GCC | GGA | TAT | 48 |
|-----|-----|-----|-----|-----|-----|-----|-----|-----|-----|-----|-----|-----|-----|-----|-----|----|
| Asn | Tyr | Ala | Ser | His | Ala | Leu | Val | Cys | Met | Leu | Leu | Arg | Ala | Gly | Tyr |    |
| 10  |     |     |     |     | 15  |     |     |     | 20  |     |     |     |     |     | 25  |    |

| AGA | GAC | AGT | TGC | TGC | TGC | GAC | GAG | CGT | CGT | TGT | GAG | ACG | CGT | GAG | 93 |
|-----|-----|-----|-----|-----|-----|-----|-----|-----|-----|-----|-----|-----|-----|-----|----|
| Arg | Asp | Ser | Cys | Cys | Cys | Asp | Glu | Arg | Arg | Cys | Glu | Thr | Arg | Glu |    |
|     |     |     | 30  |     |     |     | 35  |     |     |     |     |     | 40  |     |    |

(2) INFORMATION FOR SEQ ID NO:9:

(i) SEQUENCE CHARACTERISTICS:
        (A) LENGTH: 31 amino acids
        (B) TYPE: amino acid
        (D) TOPOLOGY: linear (ii) MOLECULE TYPE: protein (xi) SEQUENCE DESCRIPTION: SEQ ID NO:9:

Asn Tyr Ala Ser His Ala Leu Val Cys Met Leu Leu Arg Ala Gly Tyr
 1           5                   10                  15

Arg Asp Ser Cys Cys Cys Asp Glu Arg Arg Cys Glu Thr Arg Glu
             20                  25                  30

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: unknown
        (D) TOPOLOGY: unknown (ii) MOLECULE TYPE: cDNA ( v i ) ORIGINAL SOURCE:
        ( A ) ORGANISM: TLTF ( i x ) FEATURE:
        ( A ) NAME/KEY: CDS
        ( B ) LOCATION: 1..24

( x i ) SEQUENCE DESCRIPTION: SEQ ID NO:10:

```
TTG  CGA  GGC  GAA  ACC  TAT  AAA  GAT                           24
Leu  Arg  Gly  Glu  Thr  Tyr  Lys  Asp
               3 5
```

( 2 ) INFORMATION FOR SEQ ID NO:11:

( i ) SEQUENCE CHARACTERISTICS:
                ( A ) LENGTH: 8 amino acids
                ( B ) TYPE: amino acid
                ( D ) TOPOLOGY: linear ( i i ) MOLECULE TYPE: protein ( x i ) SEQUENCE DESCRIPTION: SEQ ID NO:11:

```
Leu  Arg  Gly  Glu  Thr  Tyr  Lys  Asp
 1                    5
```

( 2 ) INFORMATION FOR SEQ ID NO:12:

( i ) SEQUENCE CHARACTERISTICS:
                ( A ) LENGTH: 15 base pairs
                ( B ) TYPE: nucleic acid
                ( C ) STRANDEDNESS: unknown
                ( D ) TOPOLOGY: unknown ( i i ) MOLECULE TYPE: cDNA ( v i ) ORIGINAL SOURCE:
                ( A ) ORGANISM: TLTF ( i x ) FEATURE:
                ( A ) NAME/KEY: CDS
                ( B ) LOCATION: 1..15

( x i ) SEQUENCE DESCRIPTION: SEQ ID NO:12:

```
GGC  CGG  TTA  TCA  TTG                                          15
Gly  Arg  Leu  Ser  Leu
     1 0
```

( 2 ) INFORMATION FOR SEQ ID NO:13:

( i ) SEQUENCE CHARACTERISTICS:
                ( A ) LENGTH: 5 amino acids
                ( B ) TYPE: amino acid
                ( D ) TOPOLOGY: linear ( i i ) MOLECULE TYPE: protein ( x i ) SEQUENCE DESCRIPTION: SEQ ID NO:13:

```
Gly  Arg  Leu  Ser  Leu
 1                    5
```

( 2 ) INFORMATION FOR SEQ ID NO:14:

( i ) SEQUENCE CHARACTERISTICS:
                ( A ) LENGTH: 43 base pairs
                ( B ) TYPE: nucleic acid
                ( C ) STRANDEDNESS: unknown
                ( D ) TOPOLOGY: unknown ( i i ) MOLECULE TYPE: cDNA ( v i ) ORIGINAL SOURCE:
                ( A ) ORGANISM: TLTF ( i x ) FEATURE:
    ( A ) NAME/KEY: CDS
    ( B ) LOCATION: 1..42

( x i ) SEQUENCE DESCRIPTION: SEQ ID NO:14:

```
CCT  CAC  TTT  ATT  GTC  ATT  TCA  CTA  AAA  AAA  AAA  AAA  AAA  AAA         42
Pro  His  Phe  Ile  Val  Ile  Ser  Leu  Lys  Lys  Lys  Lys  Lys  Lys
               10                        15

A                                                                            43
```

( 2 ) INFORMATION FOR SEQ ID NO:15:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Pro  His  Phe  Ile  Val  Ile  Ser  Leu  Lys  Lys  Lys  Lys  Lys  Lys
 1                    5                        10
```

( 2 ) INFORMATION FOR SEQ ID NO:16:

( i ) SEQUENCE CHARACTERISTICS:
        ( A ) LENGTH: 493 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: TLTF ( x i ) SEQUENCE DESCRIPTION: SEQ ID NO:16:

```
Met  Ser  Pro  Arg  Thr  Gly  Ala  Glu  Arg  Gly  Arg  Arg  Lys  Ser  Val
 1              5                        10                        15

Lys  Ala  Pro  Pro  Pro  Val  Asp  Pro  Leu  Val  Glu  Leu  Thr  Thr  Leu  Glu
               20                        25                        30

Ser  Val  His  Asp  Ala  Leu  Ala  Lys  Ala  Glu  Arg  Leu  Arg  Asn  Tyr  Phe
          35                        40                        45

Gln  Val  Glu  Arg  Asp  Lys  Val  Asn  Asp  Phe  Trp  Thr  Ile  Thr  Lys  Gly
     50                        55                        60

Glu  Val  Glu  Thr  Tyr  Arg  Asn  Arg  Leu  Phe  Asn  Ala  Glu  Ala  Ser  Ile
 65                       70                        75                        80

Glu  Glu  Leu  Glu  Arg  Ser  His  Gln  Val  Glu  Met  Lys  Val  Tyr  Lys  Gln
               85                        90                        95

Arg  Val  Arg  His  Leu  Ile  Tyr  Glu  Arg  Lys  Lys  Lys  Ala  Gln  Ala  Cys
               100                       105                       110

Gln  Asp  Glu  Ser  His  Arg  Leu  Leu  Arg  Glu  Ala  Glu  Asp  Arg  His  Leu
          115                       120                       125

Gln  Arg  Met  Asn  Glu  Ile  Gln  Ala  Lys  Leu  Gln  Gln  Asp  Gln  Gln
     130                       135                       140

Leu  Arg  Ala  Ala  Ala  Ala  Asp  His  Glu  Met  Asn  Val  Tyr  Glu  Lys  Arg
145                       150                       155                       160

Asp  Ser  His  Ser  Tyr  Met  Val  Thr  Val  Thr  Lys  Thr  Gln  Ser  His  Glu
               165                       170                       175

Lys  Glu  Leu  Ala  Arg  Leu  Gln  Val  Ser  Cys  Glu  Ala  Lys  Leu  Lys  Val
               180                       185                       190
```

Leu Arg Asp Glu Leu Glu Leu Arg Arg Arg Arg Gln Ile His Glu Ile
            195                     200                 205

Glu Glu Arg Lys Asn Glu His Ile Asn Ala Leu Ile Lys Gln His Glu
        210                 215                 220

Glu Lys Phe His Glu Met Lys Thr Tyr Tyr Asn Gln Ile Thr Thr Asn
225                     230                 235                 240

Asn Leu Glu Ile Ile His Ser Leu Lys Glu Ile Ala Gln Met Lys
                    245                 250                 255

Gln Asn Asp Glu His Asn Glu Thr Leu Met Tyr Asp Ile Asp Arg Glu
                260                 265                 270

Asn Gln Asn Leu Val Ala Pro Leu Glu Ala Gln Arg Glu Val Ala
            275                 280                 285

Glu Leu Gln Gln Lys Arg Lys Gln Asn Glu Gln Asn Lys Arg Gly Leu
        290                 295                 300

Glu Val Thr Arg Val Lys Leu Arg Ser Leu Arg Glu Glu Ile Arg Arg
305                     310                 315                 320

Gln Arg Glu Glu His Gln Ala Leu Glu Glu Arg Tyr Ala Cys Val His
                325                 330                 335

Arg Glu Arg Glu Glu Leu Lys Gly Lys Phe Glu Ser Ala Leu Arg Gln
            340                 345                 350

Ala Val Met Val Val Glu Glu Arg Asn Glu Val Leu Gln Gln Lys Leu
        355                 360                 365

Ile Glu Ser His Ala Leu Val Glu Glu Arg Asp Val Gln Leu Glu Gly
    370                 375                 380

Val Leu Arg Ala Met Asn Leu Glu Pro Lys Thr Leu Glu Leu Ile Ala
385                 390                 395                 400

Thr Glu Val Asp Glu Trp Leu Gln Arg Lys Asn Gln Leu Ile Lys Asp
                    405                 410                 415

Leu His Phe Glu Leu Lys Lys Gly Glu Lys Leu Tyr Ser Ala Thr Leu
                420                 425                 430

Leu Glu Met Glu Ser Val Ala Arg Arg Leu Thr Leu Leu His Cys His
            435                 440                 445

Val Ala Thr Leu Ser Arg Cys Cys Gly Ser His Val Gly Cys Ser Lys
        450                 455                 460

Leu Arg Leu Cys Cys Ser Ser His Ser Ala Val Gly Val Val Gly Cys
465                 470                 475                 480

Phe Phe Phe Ser Ser Val Leu Leu Pro Leu Ser Pro Phe
                485                 490

( 2 ) INFORMATION FOR SEQ ID NO:17:

( i ) SEQUENCE CHARACTERISTICS:
        ( A ) LENGTH: 467 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: TLTF ( x i ) SEQUENCE DESCRIPTION: SEQ ID NO:17:

Met Ser Pro Arg Thr Gly Ala Glu Arg Gly Gly Arg Arg Lys Ser Val
1                   5                   10                  15

Lys Ala Pro Pro Pro Val Asp Pro Leu Val Glu Leu Thr Thr Leu Glu
            20                  25                  30

Ser Val His Asp Ala Leu Ala Lys Ala Glu Arg Leu Arg Asn Tyr Phe

|    |     |     |     | 35  |     |     |     | 40  |     |     |     | 45  |     |     |
|----|-----|-----|-----|-----|-----|-----|-----|-----|-----|-----|-----|-----|-----|-----|

Gln Val Glu Arg Asp Lys Val Asn Asp Phe Trp Thr Ile Thr Lys Gly
  50                  55                  60

Glu Val Glu Thr Tyr Arg Asn Arg Leu Phe Asn Ala Glu Ala Ser Ile
 65              70                  75                      80

Glu Glu Leu Glu Arg Ser His Gln Val Glu Met Lys Val Tyr Lys Gln
                 85                  90                  95

Arg Val Arg His Leu Ile Tyr Glu Arg Lys Lys Ala Gln Ala Cys
             100                 105                 110

Gln Asp Glu Ser His Arg Leu Leu Arg Glu Ala Glu Asp Arg His Leu
             115                 120                 125

Gln Arg Met Asn Glu Ile Gln Ala Lys Leu Gln Gln Asp Gln Gln
 130                 135                 140

Leu Arg Ala Ala Ala Ala Asp His Glu Met Asn Val Tyr Glu Lys Arg
 145                 150                 155                 160

Asp Ser His Ser Tyr Met Val Thr Val Thr Lys Thr Gln Ser His Glu
                 165                 170                 175

Lys Glu Leu Ala Arg Leu Gln Val Ser Cys Glu Ala Lys Leu Lys Val
             180                 185                 190

Leu Arg Asp Glu Leu Glu Leu Arg Arg Arg Gln Ile His Glu Ile
             195                 200                 205

Glu Glu Arg Lys Asn Glu His Ile Asn Ala Leu Ile Lys Gln His Glu
 210                 215                 220

Glu Lys Phe His Glu Met Lys Thr Tyr Tyr Asn Gln Ile Thr Thr Asn
 225                 230                 235                 240

Asn Leu Glu Ile Ile His Ser Leu Lys Glu Glu Ile Ala Gln Met Lys
                 245                 250                 255

Gln Asn Asp Glu His Asn Glu Thr Leu Met Tyr Asp Leu Asp Arg Glu
             260                 265                 270

Asn Gln Asn Leu Val Ala Pro Leu Glu Glu Ala Gln Arg Glu Val Ala
             275                 280                 285

Glu Leu Gln Gln Lys Arg Lys Gln Asn Glu Gln Asn Lys Arg Gly Leu
 290                 295                 300

Glu Val Thr Arg Val Lys Leu Arg Ser Leu Arg Glu Glu Ile Arg Arg
 305                 310                 315                 320

Gln Arg Glu Glu His Gln Ala Leu Glu Glu Arg Tyr Ala Cys Val His
             325                 330                 335

Arg Glu Arg Glu Glu Leu Lys Gly Lys Phe Glu Ser Ala Leu Arg Gln
             340                 345                 350

Ala Val Met Val Val Glu Glu Arg Asn Glu Val Leu Gln Gln Lys Leu
             355                 360                 365

Ile Glu Ser His Ala Leu Val Glu Glu Arg Asp Val Gln Leu Glu Gly
             370                 375                 380

Val Leu Arg Ala Met Asn Leu Glu Pro Lys Thr Leu Glu Leu Ile Ala
 385                 390                 395                 400

Thr Glu Val Asp Glu Trp Leu Gln Arg Lys Asn Gln Leu Ile Lys Asp
                 405                 410                 415

Leu His Phe Glu Leu Lys Lys Gly Glu Lys Leu Tyr Ser Ala Thr Leu
             420                 425                 430

Leu Glu Met Glu Ser Val Ala Arg Arg Leu Thr Leu Leu His Cys His
             435                 440                 445

Val Ala Thr Leu Ser Arg Cys Cys Gly Ser His Val Gly Cys Ser Lys
 450                 455                 460

Leu Arg Leu
465

(2) INFORMATION FOR SEQ ID NO:18:

(i) SEQUENCE CHARACTERISTICS:
        (A) LENGTH: 452 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: TLTF (xi) SEQUENCE DESCRIPTION: SEQ ID NO:18:

```
Met Ser Pro Arg Thr Gly Ala Glu Arg Gly Gly Arg Arg Lys Ser Val
  1               5                  10                  15

Lys Ala Pro Pro Pro Val Asp Pro Leu Val Glu Leu Thr Thr Leu Glu
                 20                  25                  30

Ser Val His Asp Ala Leu Ala Lys Ala Glu Arg Leu Arg Asn Tyr Phe
             35                  40                  45

Gln Val Glu Arg Asp Lys Val Asn Asp Phe Trp Thr Ile Thr Lys Gly
     50                  55                  60

Glu Val Glu Thr Tyr Arg Asn Arg Leu Phe Asn Ala Glu Ala Ser Ile
 65                  70                  75                  80

Glu Glu Leu Glu Arg Ser His Gln Val Glu Met Lys Val Tyr Lys Gln
                 85                  90                  95

Arg Val Arg His Leu Ile Tyr Glu Arg Lys Lys Lys Ala Gln Ala Cys
                100                 105                 110

Gln Asp Glu Ser His Arg Leu Leu Arg Glu Ala Glu Asp Arg His Leu
            115                 120                 125

Gln Arg Met Asn Glu Ile Gln Ala Lys Leu Gln Gln Asp Gln Gln
    130                 135                 140

Leu Arg Ala Ala Ala Ala Asp His Glu Met Asn Val Tyr Glu Lys Arg
145                 150                 155                 160

Asp Ser His Ser Tyr Met Val Thr Val Thr Lys Thr Gln Ser His Glu
                165                 170                 175

Lys Glu Leu Ala Arg Leu Gln Val Ser Cys Glu Ala Lys Leu Lys Val
            180                 185                 190

Leu Arg Asp Glu Leu Glu Leu Arg Arg Arg Gln Ile His Glu Ile
            195                 200                 205

Glu Glu Arg Lys Asn Glu His Ile Asn Ala Leu Ile Lys Gln His Glu
    210                 215                 220

Glu Lys Phe His Glu Met Lys Thr Tyr Tyr Asn Gln Ile Thr Thr Asn
225                 230                 235                 240

Asn Leu Glu Ile Ile His Ser Leu Lys Glu Glu Ile Ala Gln Met Lys
                245                 250                 255

Gln Asn Asp Glu His Asn Glu Thr Leu Met Tyr Asp Ile Asp Arg Glu
            260                 265                 270

Asn Gln Asn Leu Val Ala Pro Leu Glu Glu Ala Gln Arg Glu Val Ala
    275                 280                 285

Glu Leu Gln Gln Lys Arg Lys Gln Asn Glu Gln Asn Lys Arg Gly Leu
    290                 295                 300

Glu Val Thr Arg Val Lys Leu Arg Ser Leu Arg Glu Glu Ile Arg Arg
305                 310                 315                 320

Gln Arg Glu Glu His Gln Ala Leu Glu Glu Arg Tyr Ala Cys Val His
```

|     |     |     |     | 325 |     |     |     |     | 330 |     |     |     |     | 335 |
| --- | --- | --- | --- | --- | --- | --- | --- | --- | --- | --- | --- | --- | --- | --- |
| Arg | Glu | Arg | Glu<br>340 | Glu | Leu | Lys | Gly | Lys<br>345 | Phe | Glu | Ser | Ala | Leu<br>350 | Arg | Gln |
| Ala | Val | Met | Val<br>355 | Val | Glu | Glu | Arg | Asn<br>360 | Glu | Val | Leu | Gln<br>365 | Gln | Lys | Leu |
| Ile | Glu | Ser | His<br>370 | Ala | Leu | Val<br>375 | Glu | Glu | Arg | Asp | Val<br>380 | Gln | Leu | Glu | Gly |
| Val<br>385 | Leu | Arg | Ala | Met | Asn<br>390 | Leu | Glu | Pro | Lys | Thr<br>395 | Leu | Glu | Leu | Ile | Ala<br>400 |
| Thr | Glu | Val | Asp | Glu<br>405 | Trp | Leu | Gln | Arg | Lys<br>410 | Asn | Gln | Leu | Ile | Lys<br>415 | Asp |
| Leu | His | Phe | Glu<br>420 | Leu | Lys | Lys | Gly | Glu<br>425 | Lys | Leu | Tyr | Ser | Ala<br>430 | Thr | Leu |
| Leu | Glu | Met<br>435 | Glu | Ser | Val | Ala | Arg<br>440 | Arg | Leu | Thr | Leu | Leu<br>445 | His | Cys | His |
| Val | Ala | Thr<br>450 | Leu |

( 2 ) INFORMATION FOR SEQ ID NO:19:

( i ) SEQUENCE CHARACTERISTICS:
        ( A ) LENGTH: 311 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: TLTF ( x i ) SEQUENCE DESCRIPTION: SEQ ID NO:19:

| Met<br>1 | Ser | Pro | Arg | Thr<br>5 | Gly | Ala | Glu | Arg | Gly<br>10 | Gly | Arg | Arg | Lys | Ser<br>15 | Val |
| --- | --- | --- | --- | --- | --- | --- | --- | --- | --- | --- | --- | --- | --- | --- | --- |
| Lys | Ala | Pro | Pro<br>20 | Pro | Val | Asp | Pro | Leu<br>25 | Val | Glu | Leu | Thr | Thr<br>30 | Leu | Glu |
| Ser | Val | His<br>35 | Asp | Ala | Leu | Ala | Ala<br>40 | Glu | Arg | Leu | Arg<br>45 | Asn | Tyr | Phe |
| Gln | Val<br>50 | Glu | Arg | Asp | Lys | Val<br>55 | Asn | Asp | Phe | Trp | Thr<br>60 | Ile | Thr | Lys | Gly |
| Glu<br>65 | Val | Glu | Thr | Tyr | Arg<br>70 | Asn | Arg | Leu | Phe | Asn<br>75 | Ala | Glu | Ala | Ser | Ile<br>80 |
| Glu | Glu | Leu | Glu | Arg<br>85 | Ser | His | Gln | Val | Glu<br>90 | Met | Lys | Val | Tyr | Lys<br>95 | Gln |
| Arg | Val | Arg | His<br>100 | Leu | Ile | Tyr | Glu | Arg<br>105 | Lys | Lys | Lys | Ala | Gln<br>110 | Ala | Cys |
| Gln | Asp | Glu<br>115 | Ser | His | Arg | Leu | Leu<br>120 | Arg | Glu | Ala | Glu | Asp<br>125 | Arg | His | Leu |
| Gln | Arg<br>130 | Met | Asn | Glu | Ile | Gln<br>135 | Ala | Lys | Leu | Gln | Gln<br>140 | Gln | Asp | Gln | Gln |
| Leu<br>145 | Arg | Ala | Ala | Ala | Ala<br>150 | Asp | His | Glu | Met | Asn<br>155 | Val | Tyr | Glu | Lys | Arg<br>160 |
| Asp | Ser | His | Ser | Tyr<br>165 | Met | Val | Thr | Val | Thr<br>170 | Lys | Thr | Gln | Ser | His<br>175 | Glu |
| Lys | Glu | Leu | Ala<br>180 | Arg | Leu | Gln | Val | Ser<br>185 | Cys | Glu | Ala | Lys | Ile<br>190 | Lys | Val |
| Leu | Arg | Asp<br>195 | Glu | Leu | Glu | Leu | Arg<br>200 | Arg | Arg | Gln | Ile<br>205 | His | Glu | Ile |

-continued

Glu Glu Arg Lys Asn Glu His Ile Asn Ala Leu Ile Lys Gln His Glu
210 215 220

Glu Lys Phe His Glu Met Lys Thr Tyr Tyr Asn Gln Ile Thr Thr Asn
225 230 235 240

Asn Leu Glu Ile Ile His Ser Leu Lys Glu Glu Ile Ala Gln Met Lys
245 250 255

Gln Asn Asp Glu His Asn Glu Thr Leu Met Tyr Asp Ile Asp Arg Glu
260 265 270

Asn Gln Asn Leu Val Ala Pro Leu Glu Glu Ala Gln Arg Glu Val Ala
275 280 285

Glu Leu Gln Gln Lys Arg Lys Gln Asn Glu Gln Asn Lys Arg Gly Leu
290 295 300

Glu Val Thr Arg Val Lys Leu
305 310

( 2 ) INFORMATION FOR SEQ ID NO:20:

( i ) SEQUENCE CHARACTERISTICS:
( A ) LENGTH: 145 amino acids
( B ) TYPE: amino acid
( C ) STRANDEDNESS: single
( D ) TOPOLOGY: linear ( i i ) MOLECULE TYPE: peptide ( v i ) ORIGINAL SOURCE:
( A ) ORGANISM: TLTF ( x i ) SEQUENCE DESCRIPTION: SEQ ID NO:20:

Met Ser Pro Arg Thr Gly Ala Glu Arg Gly Gly Arg Arg Lys Ser Val
1 5 10 15

Lys Ala Pro Pro Pro Val Asp Pro Leu Val Glu Leu Thr Thr Leu Glu
20 25 30

Ser Val His Asp Ala Leu Ala Lys Ala Glu Arg Leu Arg Asn Tyr Phe
35 40 45

Gln Val Glu Arg Asp Lys Val Asn Asp Phe Trp Thr Ile Thr Lys Gly
50 55 60

Glu Val Glu Thr Tyr Arg Asn Arg Leu Phe Asn Ala Glu Ala Ser Ile
65 70 75 80

Glu Glu Leu Glu Arg Ser His Gln Val Glu Met Lys Val Tyr Lys Gln
85 90 95

Arg Val Arg His Leu Ile Tyr Glu Arg Lys Lys Lys Ala Gln Ala Cys
100 105 110

Gln Asp Glu Ser His Arg Leu Leu Arg Glu Ala Glu Asp Arg His Leu
115 120 125

Gln Arg Met Asn Glu Ile Gln Ala Lys Leu Gln Gln Gln Asp Gln Gln
130 135 140

Leu
145